(12) United States Patent  
Ostroff et al.

(10) Patent No.: US 8,050,754 B2
(45) Date of Patent: Nov. 1, 2011

(54) METHOD FOR DISCRIMINATING BETWEEN VENTRICULAR AND SUPRAVENTRICULAR ARRHYTHMIAS

(75) Inventors: Alan H. Ostroff, San Clemente, CA (US); Jay A. Warren, San Juan Capistrano, CA (US); Gust H. Bardy, Carnation, WA (US)

(73) Assignee: Cameron Health, Inc., San Clemente, CA (US)

( * ) Notice: Subject to any disclaimer, the term of this patent is extended or adjusted under 35 U.S.C. 154(b) by 469 days.

(21) Appl. No.: 12/259,926

(22) Filed: Oct. 28, 2008

(65) Prior Publication Data

US 2009/0054938 A1 Feb. 26, 2009

Related U.S. Application Data

(63) Continuation of application No. 11/120,258, filed on May 2, 2005, now Pat. No. 7,444,182, and a continuation of application No. 12/029,272, filed on Feb. 11, 2008, which is a continuation of application No. 10/856,084, filed on May 27, 2004, now Pat. No. 7,330,757.

(60) Provisional application No. 60/474,323, filed on May 29, 2003.

(51) Int. Cl.
*A61N 1/00* (2006.01)
(52) U.S. Cl. ............................................ 607/5; 600/515
(58) Field of Classification Search ................ 607/4–28; 600/508–520
See application file for complete search history.

(56) References Cited

U.S. PATENT DOCUMENTS 5,873,897 A 2/1999 Armstrong et al.
2004/0093037 A1 5/2004 Henry

OTHER PUBLICATIONS

JPO Allowance (Sep.13, 2010), Response/Amendment (Aug. 2, 2010), and JPO Action (Mar. 2, 2010) for related/family application filed in Japan (JP App. No. 2006-533540, Issued as JP 4,615,518).

*Primary Examiner* — Scott Getzow
(74) *Attorney, Agent, or Firm* — Pramudji Law Group PLLC; Ari Pramudji; Mark Schroeder

(57) ABSTRACT

The present invention is directed toward a detection architecture for use in implantable cardiac rhythm devices. The detection architecture of the present invention provides methods and devices for discriminating between arrhythmias. Moreover, by exploiting the enhanced specificity in the origin of the identified arrhythmia, the detection architecture can better discriminate between rhythms appropriate for device therapy and those that are not.

12 Claims, 30 Drawing Sheets

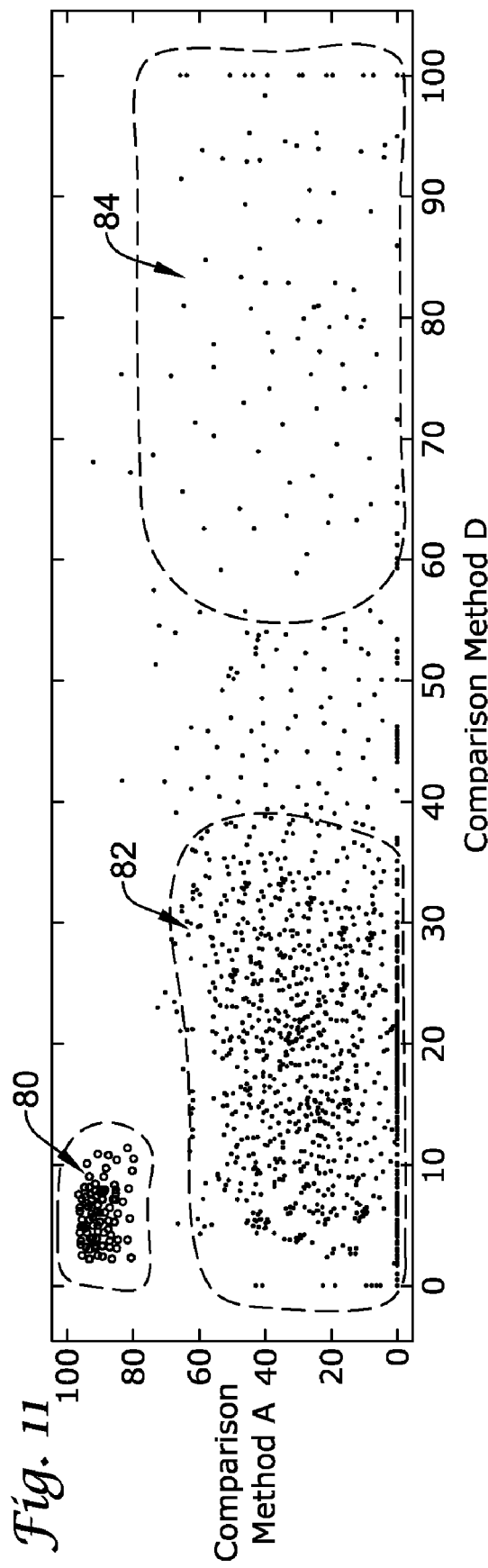
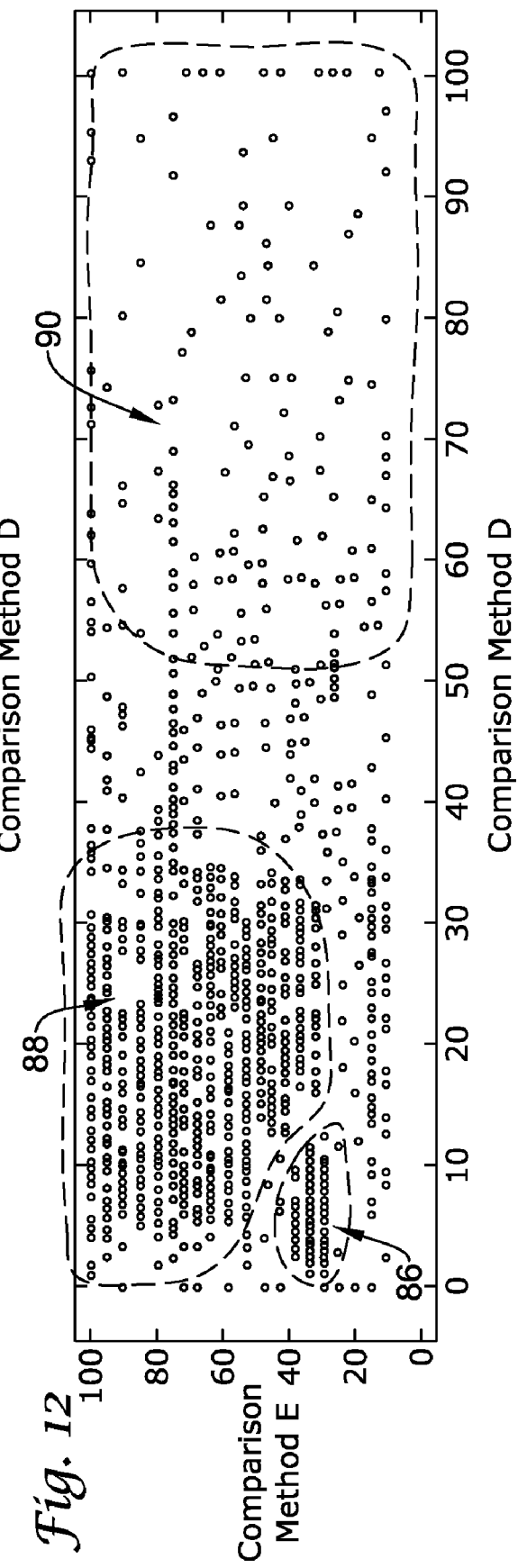

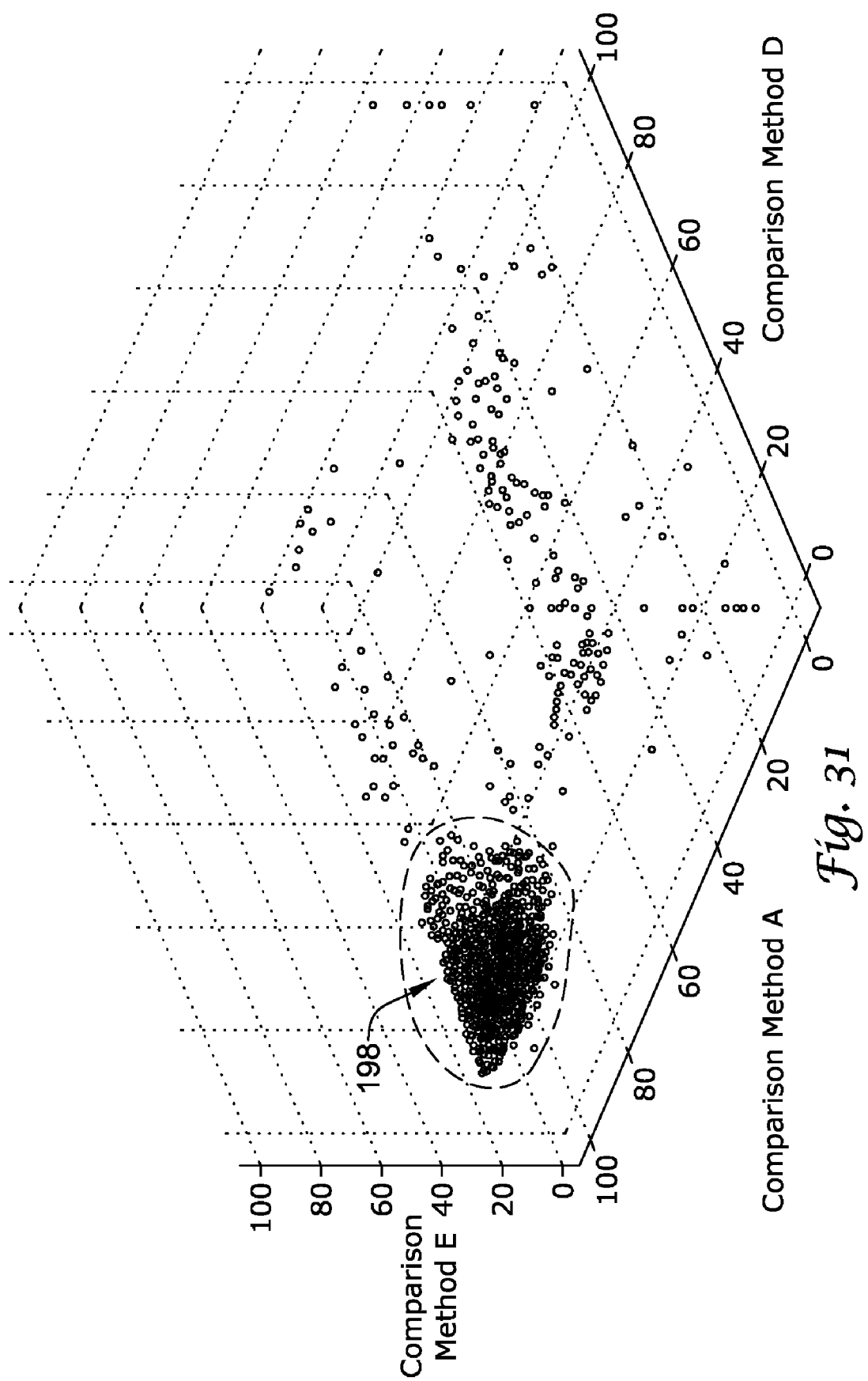

METHOD FOR DISCRIMINATING BETWEEN VENTRICULAR AND SUPRAVENTRICULAR ARRHYTHMIAS

RELATED APPLICATIONS

This application is a continuation of U.S. patent application Ser. No. 11/120,258 (now U.S. Pat. No. 7,444,182) and Ser. No. 12/029,272 (published as U.S. 2008-0132965 A1), filed May 2, 2005 and Feb. 11, 2008, respectively, which are continuations of U.S. patent application Ser. No. 10/856,084, filed May 27, 2004, now U.S. Pat. No. 7,330,757, which claims the benefit of and priority to U.S. Provisional Application Ser. No. 60/474,323, filed May 29, 2003, each of which is titled METHOD FOR DISCRIMINATING BETWEEN VENTRICULAR AND SUPRAVENTRICULAR ARRHYTHMIAS; the disclosures of which are incorporated herein by reference.

This application is related to U.S. patent application Ser. No. 12/122,432, filed May 16, 2008, which is a continuation of U.S. application Ser. No. 10/863,599, filed Jun. 8, 2004, now U.S. Pat. No. 7,379,772, which is a continuation of U.S. patent application Ser. No. 09/990,510, filed Nov. 21, 2001, now U.S. Pat. No. 6,754,528, each of which is titled APPARATUS AND METHOD OF ARRHYTHMIA DETECTION IN A SUBCUTANEOUS IMPLANTABLE CARDIOVERTER/DEFIBRILLATOR.

This application is also related to U.S. patent application Ser. No. 11/120,284, filed May 2, 2005, now U.S. Pat. No. 7,627,367, and titled MULTIPLE ELECTRODE VECTORS FOR IMPLANTABLE CARDIAC TREATMENT DEVICES, which is a continuation of U.S. patent application Ser. No. 10/901,258, filed Jul. 27, 2004, now U.S. Pat. No. 7,392,085, and titled MULTIPLE ELECTRODE VECTORS FOR IMPLANTABLE CARDIAC TREATMENT DEVICES. Further, this application is related to U.S. patent application Ser. No. 12/144,462, filed Jun. 23, 2008, now published as U.S. Pub. Pat. App. No. 2008-0275521, and titled VECTOR SWITCHING IN AN IMPLANTABLE CARDIAC STIMULUS SYSTEM, which is a divisional of U.S. patent application Ser. No. 10/901,258, filed Jul. 27, 2004, now U.S. Pat. No. 7,392,085, and titled MULTIPLE ELECTRODE VECTORS FOR IMPLANTABLE CARDIAC TREATMENT DEVICES.

FIELD

The present invention relates generally to a method and means for discriminating between cardiac rhythms appropriate for therapy using an implantable cardioverter defibrillator. More particularly, the present invention relates to a detection architecture having a detection enhancement operator that discriminates between supraventricular arrhythmias and ventricular arrhythmias.

BACKGROUND

Effective, efficient systemic circulation depends on proper cardiac function. Proper cardiac function, in turn, relies on the synchronized contractions of the heart at regular intervals. When normal cardiac rhythm is initiated by the sinoatrial node, the heart is said to be in sinus rhythm. However, when the heart experiences irregularities in its coordinated contraction, due to electrophysiologic abnormalities that are either inherited, induced, or caused by disease, the heart is denoted to be arrhythmic. The resulting cardiac arrhythmia impairs cardiac efficiency and can be a potential life threatening event.

In a heart monitoring system it is often desirable to distinguish between ventricular complexes that are conducted by the intrinsic conduction system from the atria, and ventricular complexes that originate in the ventricle. Cardiac arrhythmias arising from the atria of the heart are called supraventricular tachyarrhythmias (SVTs). Cardiac arrhythmias arising from the ventricular region of the heart are called ventricular tachyarrhythmias (VTs). SVTs and VTs are morphologically and physiologically distinct events. VTs take many forms, including ventricular fibrillation and ventricular tachycardia. Ventricular fibrillation is a condition denoted by extremely rapid, nonsynchronous, and ineffective contractions of the ventricles where the ventricular complexes of ventricular fibrillation arise from multiple locations. This condition is fatal unless the heart is returned to sinus rhythm within a few minutes. Ventricular tachycardia are conditions denoted by a rapid heart beat in excess of 120 beats per minute, but frequently as high as 150 to 350 beats per minute, that has its origin in a single location within the ventricle. This location, which is frequently abnormal cardiac tissue, typically results from damage to the ventricular myocardium from a myocardial infarction or some other heart muscle disease process. Ventricular tachycardia can and frequently does degenerate into ventricular fibrillation.

SVTs also take many forms, including atrial fibrillation, sinus tachycardia and atrial flutter. These conditions are characterized by rapid contractions of the atria. Besides being hemodynamically inefficient, the rapid contractions of the atria can also result in an elevated ventricular rate. This occurs when the aberrant electrical impulse in the atria are transmitted to the ventricles via the intrinsic conduction system. Although an SVT can result in significant symptoms for the patient, it is usually not life threatening.

Transvenous implantable cardioverter/defibrillators (transvenous ICDs) have been established as an effective treatment for patients with serious ventricular tachyarrhythmias. Transvenous ICDs are able to recognize and treat tachyarrhythmias with a variety of therapies. These therapies range from providing anti-tachycardia pacing or cardioversion energy for treating ventricular tachycardia to high energy shock for treating ventricular fibrillation. Usually, the transvenous ICD delivers these therapies in sequence starting with anti-tachycardia pacing and then proceeding to cardioversion (or low) energy and then, finally, high energy shocks. Sometimes only one of these is selected depending upon the tachyarrhythmia detected. This sequence or selection of therapy is called "tiered" therapy. To effectively deliver these treatments, the ICD must first classify the type of tachyarrhythmia that is occurring, after which appropriate therapy is provided to the heart. A problem arises, however, when the ICD delivers therapy to what was mistakenly classified as a ventricular tachycardia, but was actually a high ventricular rate caused and sustained by an SVT.

A major limitation of both past and present transvenous ICDs is inaccuracy in differentiating tachycardias requiring therapy, and tachycardias for which therapy is not appropriate. Inappropriate electrical therapy from currently available commercial and investigational devices has been reported during documented periods of sinus rhythm, sinus tachycardia and supraventricular tachycardias including atrial flutter and atrial fibrillation.

Besides being painful, when a transvenous ICD delivers inappropriate treatment to a patient, it is extremely disconcerting to the patient. Moreover, it can induce worse cardiac arrhythmias and even lead to a deterioration in cardiac contraction strength. Accurate discrimination of an SVT versus a potentially lethal ventricular tachycardia is, therefore, an important factor in ensuring that appropriate therapy is delivered to an arrhythmic heart.

For the reasons stated above, and for other reasons stated below, which will become apparent to those skilled in the art upon reading and understanding the present specification, there is a need in the art for providing a reliable system to discriminate between SVT and ventricular tachycardia and SVT and ventricular fibrillation.

SUMMARY

The detection architecture of the present invention provides methods and means for discriminating between arrhythmias. In exemplary embodiments of the present invention, the detection architecture uses various methods to direct therapy toward the treatment of ventricular arrhythmias. The present invention compares specific attributes of a sensed cardiac complex to a stored cardiac template. In particular embodiments, the stored cardiac template is updated following each sensed beat.

The present invention may also utilize multiple templates and multiple vector views to compare specific attributes of the sensed cardiac complex in order to discriminate between rhythms. In particular embodiments, the present invention may capture different sensing or vector views and compare the sensed cardiac complex to its corresponding stored template.

In particular embodiments of the present invention, a series of operations are performed that systematically eliminate possible arrhythmias until the identified arrhythmia is accurately classified. The classification of the arrhythmia is particularly aided by the present invention's ability to accurately determine the origin of the identified arrhythmia. Additionally, by exploiting the enhanced specificity in identifying the origin of the arrhythmia, the detection architecture can better discriminate between rhythms appropriate for device therapy and those that are not.

Furthermore, the present invention's ability to discern particular atrial arrhythmias permits the present invention to be used in treating particular atrial arrhythmias, or other arrhythmias that require treatment, as well. For example, the detection architecture of the present invention may be used in devices where it is desirable to discriminate and treat particular supraventricular tachycardias. And lastly, as a result of the above-described improvements, the timing associated with applying appropriate therapy may be a function of the rhythm identified and the malignancy of the identified rhythm.

BRIEF DESCRIPTION OF THE DRAWINGS

FIG. 11 depicts a graph showing the Boolean results on the sampled electrocardiogram using comparison method A and comparison method D;

FIG. 12 depicts a graph showing the Boolean results on the sampled electrocardiogram using comparison method E and comparison method D;

FIGS. 30 and 31 depict graphs illustrating how the present invention may be utilized to discriminate supraventricular arrhythmias.

DETAILED DESCRIPTION

The following detailed description should be read with reference to the drawings, in which like elements in different drawings are numbered identically. The drawings, which are not necessarily to scale, depict selected embodiments and are not intended to limit the scope of the invention. Those skilled in the art will recognize that many of the examples provided have suitable alternatives that may be utilized.

The present invention is generally related to ICD systems that provide therapy for patient's experiencing particular arrhythmias. The present invention is directed toward detection architectures for use in cardiac rhythm devices. In particular, the present invention is suited for ICD systems capable of detecting and defibrillating harmful arrhythmias. Although the detection architecture is intended primarily for use in an implantable medical device that provides defibrillation therapy, the invention is also applicable to cardiac rhythm devices (including external devices) directed toward anti-tachyarrhythmia (ATP) therapy, pacing, and other cardiac rhythm devices capable of performing a combination of therapies to treat rhythm disorders.

Figure 1A:
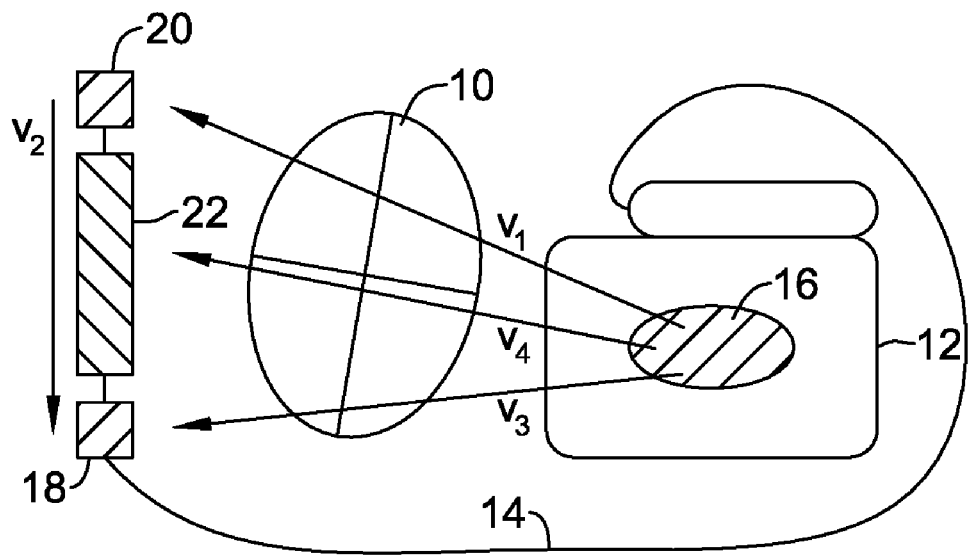
FIGS. 1A-1B illustrate, respectively, representative subcutaneous and intravenous ICD systems.
Figure 1B:
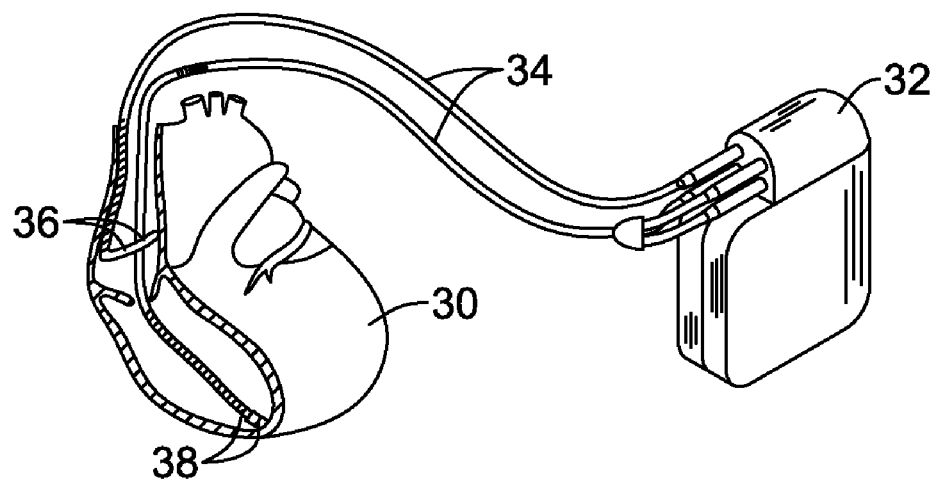

To date, ICD systems have been transvenous systems implanted generally as shown in FIG. 1B, however, as further explained herein, the present invention is also adapted to function with a subcutaneous ICD system as shown in FIG. 1A.

FIG. 1A illustrates a subcutaneously placed ICD system. In this illustrative embodiment, the heart 10 is monitored using a canister 12 coupled to a lead system 14. The canister 12 may include an electrode 16 thereon, while the lead system 14 connects to sensing electrodes 18, 20, and a coil electrode 22 that may serve as a shock or stimulus delivery electrode as well as a sensing electrode. The various electrodes define a number of sensing vectors V1, V2, V3, V4. It can be seen that each vector provides a different vector "view" of the heart's 10 electrical activity. The system may be implanted subcutaneously as illustrated, for example, in U.S. Pat. Nos. 6,647, 292 and 6,721,597, the disclosures of which are both incorporated herein by reference. By subcutaneous placement, it is meant that electrode placement does not require insertion of an electrode into a heart chamber, the heart muscle, or the patient's vasculature.

FIG. 1B illustrates a transvenous ICD system. The heart 30 is monitored and treated by a system including a canister 32 coupled to a lead system 34 including atrial electrodes 36 and ventricular electrodes 38. A number of configurations for the electrodes may be used, including placement within the heart, adherence to the heart, or disposition within the patient's vasculature. For example, Olson et al., in U.S. Pat. No. 6,731,978, illustrate electrodes disposed in each chamber of the heart for sensing, as well as shocking electrodes in addition to the sensing electrodes. While Olsen et al. make use of atrial event counts within periods defined by ventricular events relying on near field sensing, the present invention has identified distinct methods from these that, in various embodiments, provide improved sensing both in terms of capturing deleterious cardiac events and reducing false positives and unnecessary shocks.

The detection architecture of the present invention provides a method and means for discriminating between arrhythmias. Moreover, by exploiting the enhanced specificity in the origin of the identified arrhythmia, the detection architecture can better discriminate between rhythms appropriate for device therapy and those that are not. In exemplary embodiments of the present invention, the detection architecture uses various techniques illustrated herein to direct therapy toward the treatment of ventricular arrhythmias. However, the present invention's ability to discern particular atrial arrhythmias permits the present invention to be used in treating particular atrial arrhythmias, or other arrhythmias that require treatment, as well. For example, the detection architecture of the present invention may be used in devices where it is desirable to discriminate and treat particular supraventricular tachycardias. Furthermore, the timing associated with applying appropriate therapy may be a function of the rhythm identified and the malignancy of the identified rhythm.

In some embodiments, a detection enhancement operator is included. The detection enhancement operator may be engaged continuously, or become active in response to an event or a combination of events. In certain embodiments, the detection enhancement may be engaged by identifying particular rhythm patterns (i.e., long-short-long intervals). Other events capable of triggering the detection enhancement include the patient's cardiac rate, or discernable deviations in the cardiac rate (i.e., reduction in heart rate variability). For example, in single or multi lead systems (whether subcutaneous, epicardial or transvenous), these rate deviations may be identified by an abruptly accelerating ventricular rate ("paroxysmal onset"). In alternative embodiments, the detection enhancement operator may be engaged by having the rate surpass a preset or dynamically adjustable rate threshold.

Figure 2:
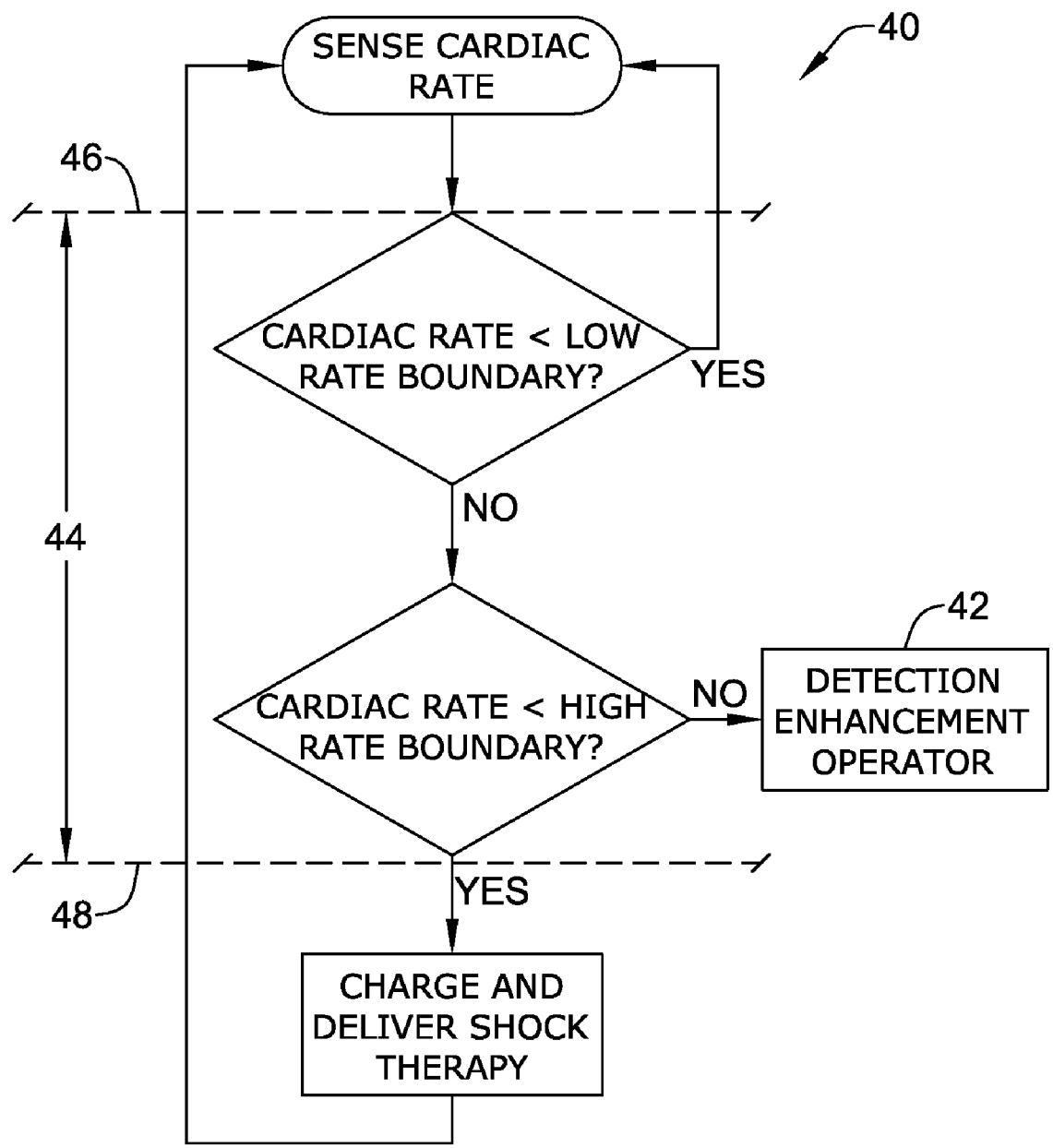
FIG. 2 shows in block form an illustrative embodiment including a representation of how a detection enhancement operator may be engaged by a rate triggering event.

FIG. 2 illustrates an embodiment 40 of the present invention showing how the detection enhancement operator 42 may be engaged by a rate triggering event. In the embodiment illustrated, a rate triggering enhancement zone 44 is formed between a low rate boundary 46 and a high rate boundary 48. The low rate boundary 46 represents the ceiling for rates failing to trigger the detection enhancement operator 42. Similarly, the high rate boundary 48 represents the floor for rates requiring therapy. Thus, only rates between the low rate boundary 46 and the high rate boundary 48 (the rate triggering enhancement zone 44) are capable of triggering the detection enhancement operator 42. Rates exceeding the high rate boundary 48 are presumptively rates that require therapy, and therefore, the detection enhancement is bypassed.

The "cardiac rate" may be determined by measuring the interval between successive cardiac complexes. For example, the count may be determined by measuring the interval between successive R-waves. This example is in no way exhaustive as numerous alternative methods for calculating cardiac rate are known to those skilled in the art.

Regardless of how the cardiac rate is monitored, high and low cardiac rate threshold boundaries may be used. Examples of these thresholds are shown in the illustrative detection enhancement scheme of FIG. 2. In preferred embodiments of the present invention, the low and high rate boundaries 46, 48 are programmable between 170 bpm and 260 bpm. By adjusting the rate boundaries, the rate triggering enhancement zone 44 may be as large as 90 bpm (high rate at 260 bpm and low rate at 170 bpm) or bypassed altogether (placing the low rate boundary at 260 bpm). Although the examples above illustrate the low rate boundary being adjustable, the high rate boundary may also be adjusted. For example, the high rate boundary may be set at 240 bpm for adult patients, whereas for children, the high rate boundary may be programmed at 280 bpm.

In the embodiment illustrated in FIG. 2, the low rate boundary 46 is set at 170 bpm and the high rate boundary 48 is set at 260 bpm. If the sensed cardiac rate is below the low rate boundary 46 (or below 170 bpm), no action is taken and the detection architecture continues to sense the cardiac rate. When the cardiac rate is above the low rate boundary 46, the detection architecture then considers whether the cardiac rate is greater than the high rate boundary 48 (or above 260 bpm). If the cardiac rate is greater than the high rate boundary 48, therapy is deemed appropriate and the capacitors are charged and therapy is delivered. Once therapy is delivered, the cardiac rate is again monitored. Alternatively, if the cardiac rate is above the low rate boundary 46 and below the high rate boundary 48, the detection architecture engages the detection enhancement operator 42. The detection enhancement operator 42 aids in discriminating between arrhythmias having rates falling within the programmed rate triggering enhancement zone 44. The function of the detection enhancement operator 42 is described in detail below.

Once the detection enhancement operator 42 is engaged, the portion of the cardiac cycle relating to ventricular depolarization is evaluated mathematically and compared to a template. The mathematical comparison may be accomplished using a number of different methods (described in detail below); however, the method of comparison is generally dependent on the template used. In some embodiments, the mathematical comparison may include a numerical calculation that does not require a template, such as QRS width trends, R-wave width, and R-wave width variance. Further, in some embodiments a mathematical comparison may include an determination of whether a rate accelerating event has occurred.

An ICD system of the present invention, in a preferred embodiment, is capable of storing and using multiple templates. Templates applicable to the detection enhancement operator may include those that are static or dynamic. Static templates are cardiac complexes that are captured previously in time and stored for reference by the device. Alternatively, dynamic templates are cardiac complexes that are captured continuously and compared to the subsequently detected cardiac complex, or a cardiac complex occurring some number of complexes later in time. Regardless of whether the template is static or dynamic, the template may be a snapshot of a single cardiac complex, or alternatively, an averaging of previously sensed cardiac complexes.

An example of a static template is a stored sinus complex. The stored sinus template may be acquired in a number of different ways. For example, the stored sinus template may be a cardiac complex selected by a physician. In one embodiment, the physician may capture a cardiac complex observed when the implanted or applied device is in communication with a programmer. After the physician detects a representative sinus complex, the physician may capture the complex on the programmer and set this complex as the sinus template for comparison. In an alternate embodiment, the physician may select an artificially created sinus template. This form of template is one artificially modeled to resemble a typical sinus complex. Yet another example of a static template is a stored sinus template that automatically updates after a preset period of time, or after a preset number of sensed complexes.

Static templates can also be formed from a cardiac complex that follows a triggering event. In certain embodiments, the cardiac complex immediately following the triggering event will be stored as the template and each subsequent complex will be compared to this stored template. In alternative embodiments, a cardiac complex forming the template is captured following a preset number of beats following the triggering event. The number of beats between capturing the template and the triggering event is programmable. In these embodiments, the number of beats between the capturing of the template and the triggering event is programmable between 2 and 14 beats. It is then this later captured template that is compared to each subsequently sensed complex.

An example of a dynamic template is a template that is continuously updated after each sensed cardiac complex. Such a dynamic template enables a mathematical comparison between the most currently sensed cardiac complex and the complex immediately preceding it. Alternatively, a dynamic template can also compare the most currently sensed cardiac complex to a template that represents an average of a selected number of previously sensed cardiac complexes. To illustrate, if the dynamic template comprises an average representation of the last four sensed complexes, with the sensing of each complex the aggregate template will add the newest sensed complex and discard the oldest sensed complex. Thus, with each additionally sensed complex the aggregate template is updated.

Dynamic templates may be formed and used continuously in the present invention, or alternatively, they may be formed and used only following the observance of a triggering event. In these embodiments, once a triggering event is observed, the dynamic template is created and subsequently updated with each cardiac complex following the triggering event. In certain embodiments, this dynamic template reverts back to a stored sinus template following a preset number of beats, or after therapy is delivered. Further examples of static and dynamic templates are described herein.

Figure 3:
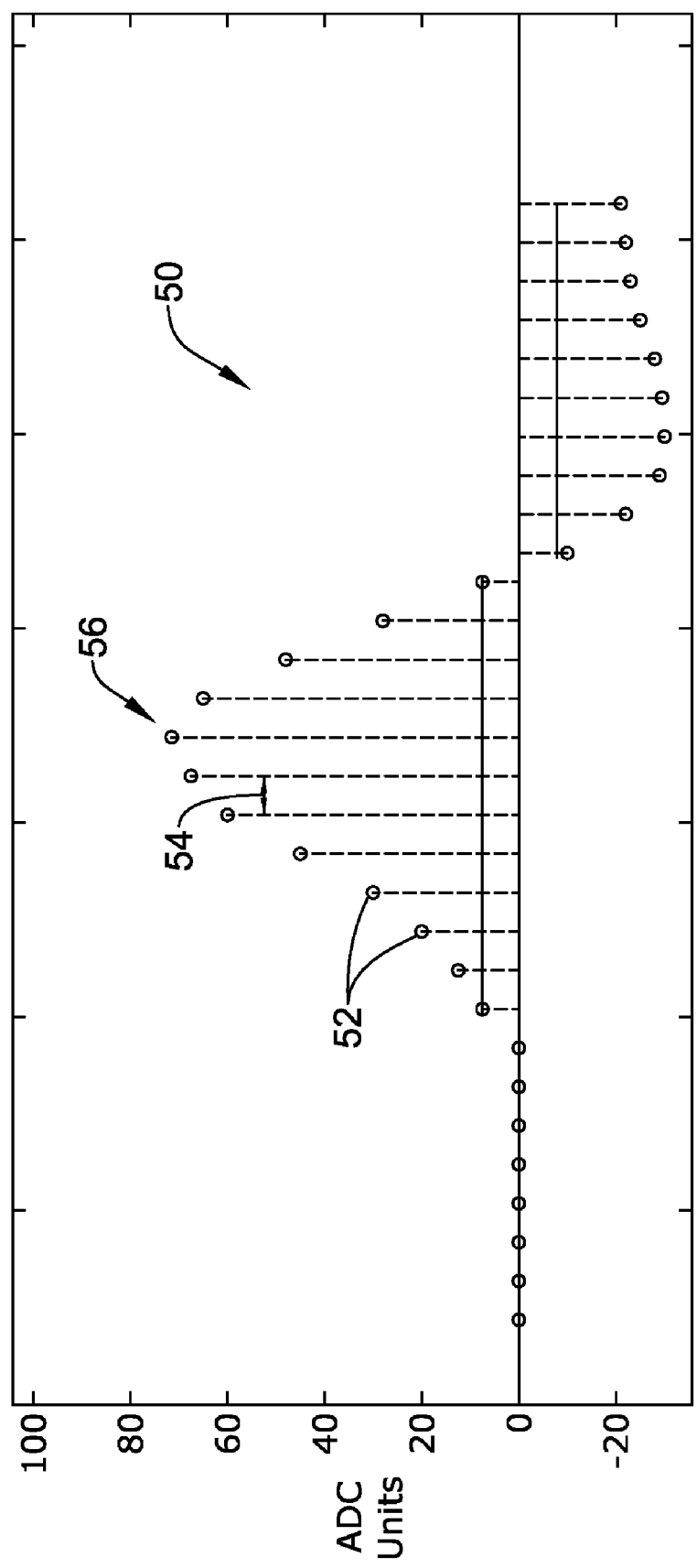
FIG. 3 shows an exemplary embodiment of a sinus template generated for use in the present invention.

An exemplary embodiment of a sinus template (for either a static or a dynamic template) generated for use in the present invention is shown in FIG. 3. The template depicted in FIG. 3 is illustrative only. The present invention is not limited in terms of how the template is formed and/or the template's particular configuration.

The template 50 depicted in FIG. 3 was generated by sampling a cardiac complex during normal sinus rhythm. The template complex 50 comprises thirty samples 52 of the single cardiac complex having a fixed sampling frequency 54 between samples. The peak 56 of the sampled normal sinus complex is placed at the center of the template 50. From the center peak 56, fifteen samples 52 are established to the left of the peak 56 and fourteen samples 52 are established to the right of the peak 56. By aligning the template 50 with a sampled cardiac complex, mathematical calculations may be performed to determine how well the sampled complex correlates with the template 50. Because the sampling frequency 54 between samples 52 is fixed, the correlation between the template 50 and the sampled complex may be mathematically evaluated. From these mathematical calculations the detection enhancement operator 42 may discern particular attributes of the sensed cardiac complex and help discriminate whether the sensed complex indicates whether treatment is indicated.

It should be noted that several of the illustrative embodiments and analyses have been prepared using a sampling rate of 256 Hertz. This sampling rate is merely illustrative, and any suitable sampling rate may be used (e.g., 128 Hertz). While the illustrative example of FIG. 3 relies upon a collection of thirty samples around a center point, other sampling methods and numbers, as well as different "windows" may be used. Greater or fewer numbers of samples may be used (at higher or lower sampling rates, if so desired), and the peak need not be placed in the center of the sampling window. Any signal feature that is amenable to repeatable sensing may be used to align the template with a sensed cardiac complex.

Along with utilizing templates that are stored at different times (static or dynamic), the detection enhancement operator 42 of the present invention may utilize templates capturing different sensing or vector views. Referring back to FIG. 1A, in this configuration, the ICD system can sense a plurality of vector views, V1, V2, V3, V4. Thus, the configuration depicted in FIG. 1A would permit at least four different sensing views for a single cardiac complex in time. Moreover, the detection enhancement operator is preferably capable of storing the four vector views individually as four different templates. The invention, however, is not limited in terms of lead or electrode types, lead or electrode configurations, or sensing templates formed from any exemplary mode or configuration. Moreover, more sensing electrodes than are shown in FIG. 1A may be added to the lead 14 and/or the canister 12 resulting in sensing vectors not described above.

The detection enhancement operator 42 of the present invention, in a preferred embodiment, can further mathematically compare acquired cardiac complexes (or their vector representations) from two views (e.g., V1 and V2) to their corresponding stored sinus template views. This configuration enhances the detection enhancement operator's ability to discern supraventricular based arrhythmias from ventricular based arrhythmias. More specifically, it is extremely unlikely that a ventricular based arrhythmia would appear the same as its stored sinus template in both views. In such an instance, at least one of the two views would indicate a morphology change, based on its origination in the ventricle, when compared to the stored sinus templates. Thus, although there may not be a discriminating difference in one view (e.g., V1) between a ventricular based arrhythmia and a stored cardiac template, by examining a second view (e.g., V2), the distinction would more likely be pronounced.

Figure 4:
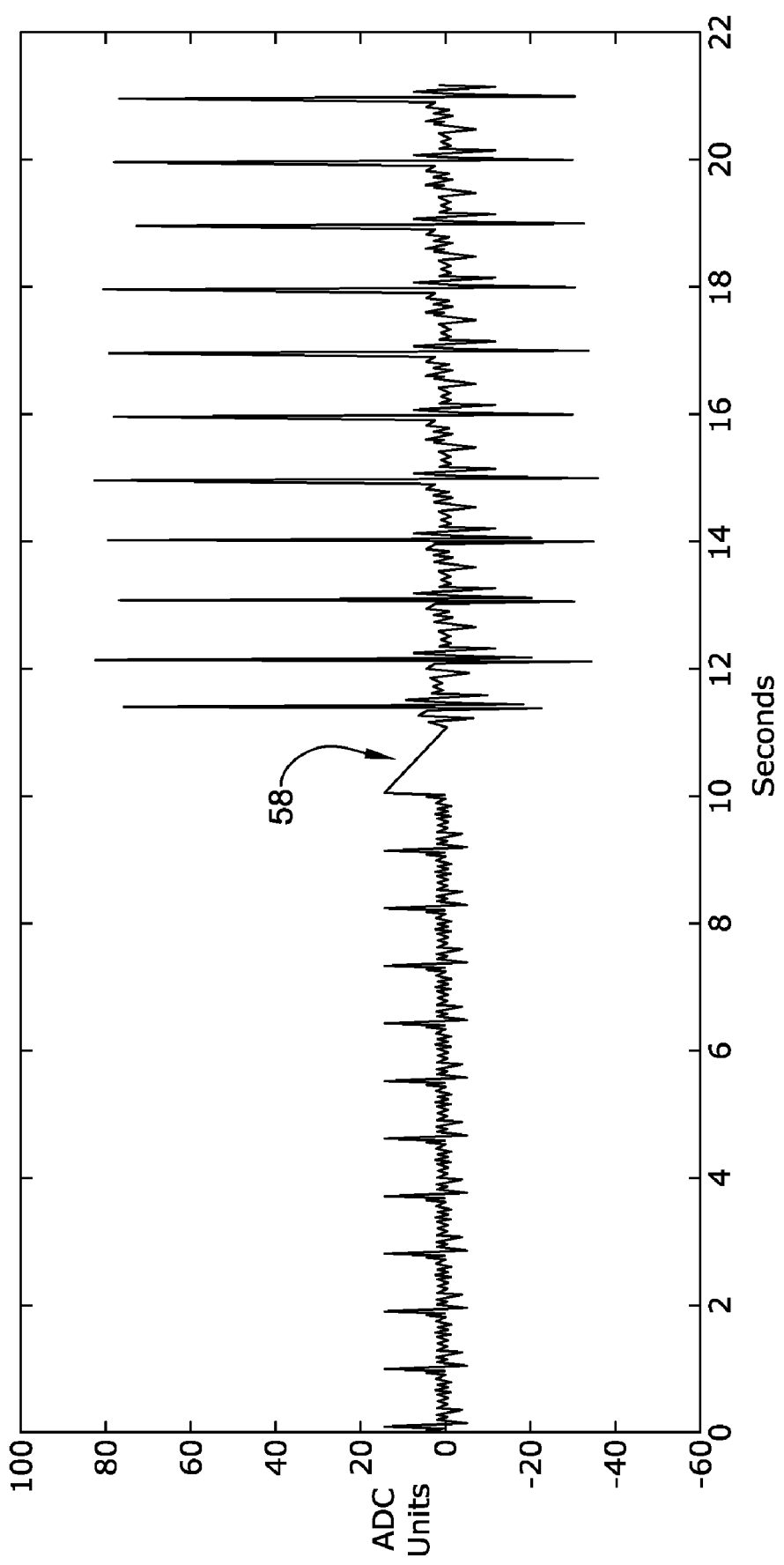
FIG. 4 illustrates the amplitude change noticed when switching between vector views.

In some preferred embodiments of the present invention, the ICD system examines vector views that are generally oriented orthogonally to one another. By using orthogonally oriented vector views, if one vector view detects only nominal electrical activity because of its orientation, a generally orthogonal vector view from the first should detect significantly larger electrical activities. FIG. 4 demonstrates this principle.

FIG. 4 illustrates twenty-three cardiac complexes. The first twelve cardiac complexes are sensed using vector view V1.

Following the twelfth cardiac complex, the ICD system begins sensing using vector view V2. Thus, the remaining eleven cardiac complexes, following the pause 58, are sensed using vector view V2.

The average electrical activity for a cardiac complex using vector view V1 in FIG. 4 is approximately 0.35 mV. In contrast, the average electrical activity for a cardiac complex using vector view V2 is approximately 1.61 mV. Therefore, a nearly 360% change in sensitivity was observed by switching between vector views. Thus, by having the ability to switch between views, a vector view may be chosen that possesses the best signal to noise ratio for R wave detection, and has the best sensitivity to observe particular attributes the detection architecture may use for discriminating between arrhythmias.

While orthogonal views provide the opportunity to capture a maximum amplitude in one vector view when a minimum amplitude is experienced in its generally orthogonal alternative vector view, having two views precisely orthogonal to one another is not a requirement of the present invention. Any relative angle may be used, and the use of multiple views is seen as one aspect of several embodiments that may improve sensing performance. If desired, even three or more views may be used in one comparison or mathematical analysis.

In some embodiments of the present invention, the ICD system continuously monitors its various vector views for the view possessing the best signal to noise ratio. This may be particularly important when the patient changes body posture or position or during alterations in respiration when signal amplitude may change for any particular vector. When a better vector view is observed, the ICD system switches to this vector view and utilizes a corresponding template to monitor individually sensed cardiac complexes. In alternative embodiments, the ICD system monitors additional vector views only when the currently used vector view experiences considerable noise or if sensing is less than optimal.

The detection enhancement operator 42 of the present invention may utilize any one of the above described templates in combination. For example, the detection enhancement operator 42 may compare a sensed cardiac complex in vector view V1 to a stored sinus template of the same vector view. At the same time, the detection enhancement operator 42 may additionally compare the most recently sensed complex to the one just previous in time in vector view V2. In this example, two vector views, a static template and a dynamic template are used in combination. Thus, the detection enhancement operator 42 may utilize several of the templates in combination to more accurately determine the type of arrhythmia and whether the arrhythmia originates from the ventricles or whether the arrhythmia is supraventricular in origin.

The detection enhancement operator 42 performs a decision making process that may be enhanced through morphology comparisons. The detection enhancement operator 42, for example, may compare the morphology of a sensed cardiac complex by one of many methods to one or more of the described templates. The mathematical comparisons between the sensed cardiac complex and the template are performed on particular attributes of the cardiac complex. In some embodiments, the attribute of comparison in a sensed complex is the slew rate, the polarity, the signal frequency content, the width of the QRS complex, the amplitude of the cardiac complex, or any combination of these or other distinguishable morphological attributes. Moreover, these attributes, and others, may be correlated to produce a reliable metric for quantifying waveform changes. Correlation Waveform Analysis (CWA) employs the correlation coefficient as a measure of similarity between the template and the waveform under analysis. The correlation coefficient can be used to produce reliable metrics to distinguish waveform changes.

Figure 5:
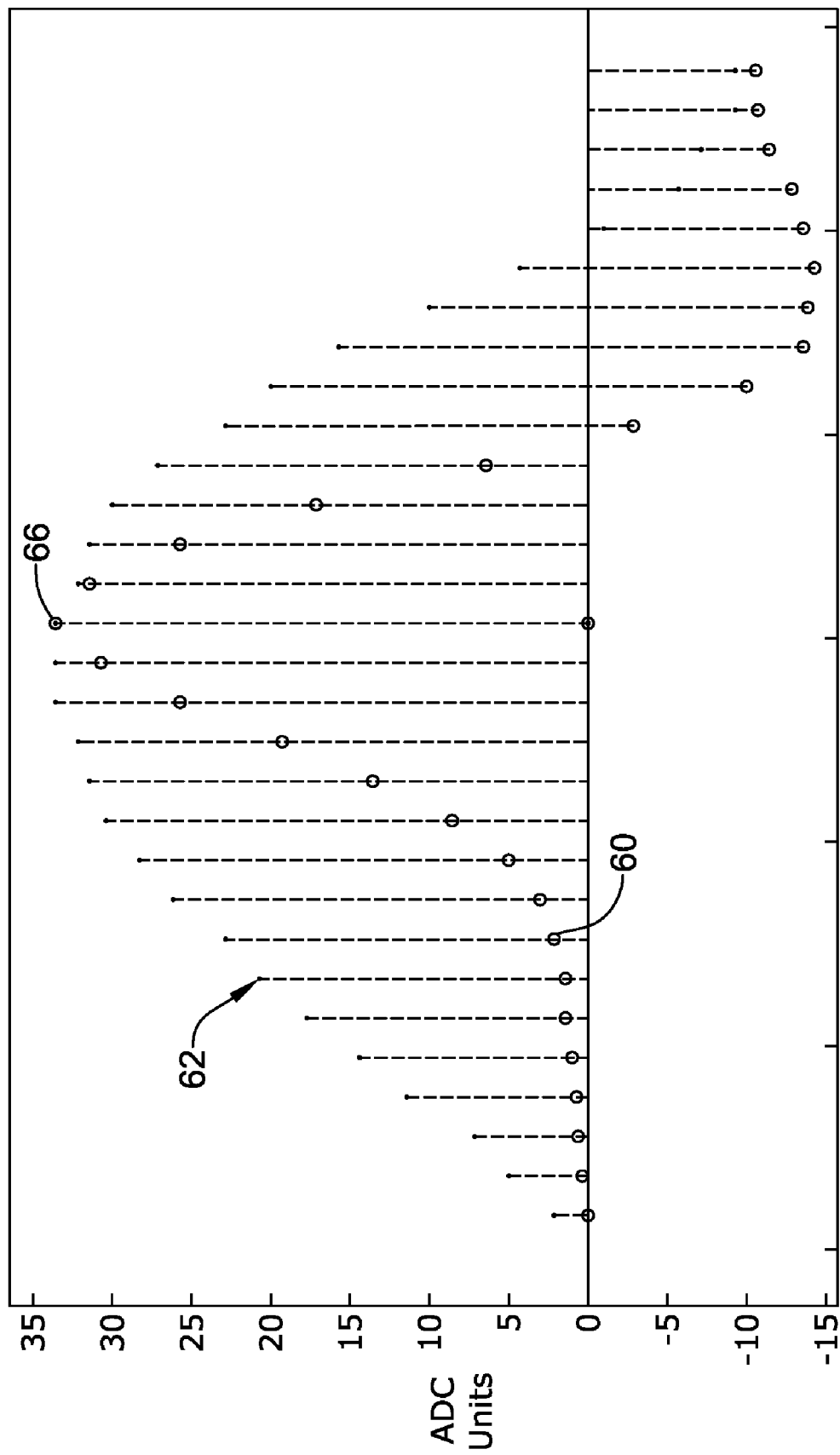
FIG. 5 shows a sensed cardiac complex that correlates poorly with a sinus template.
Figure 6:
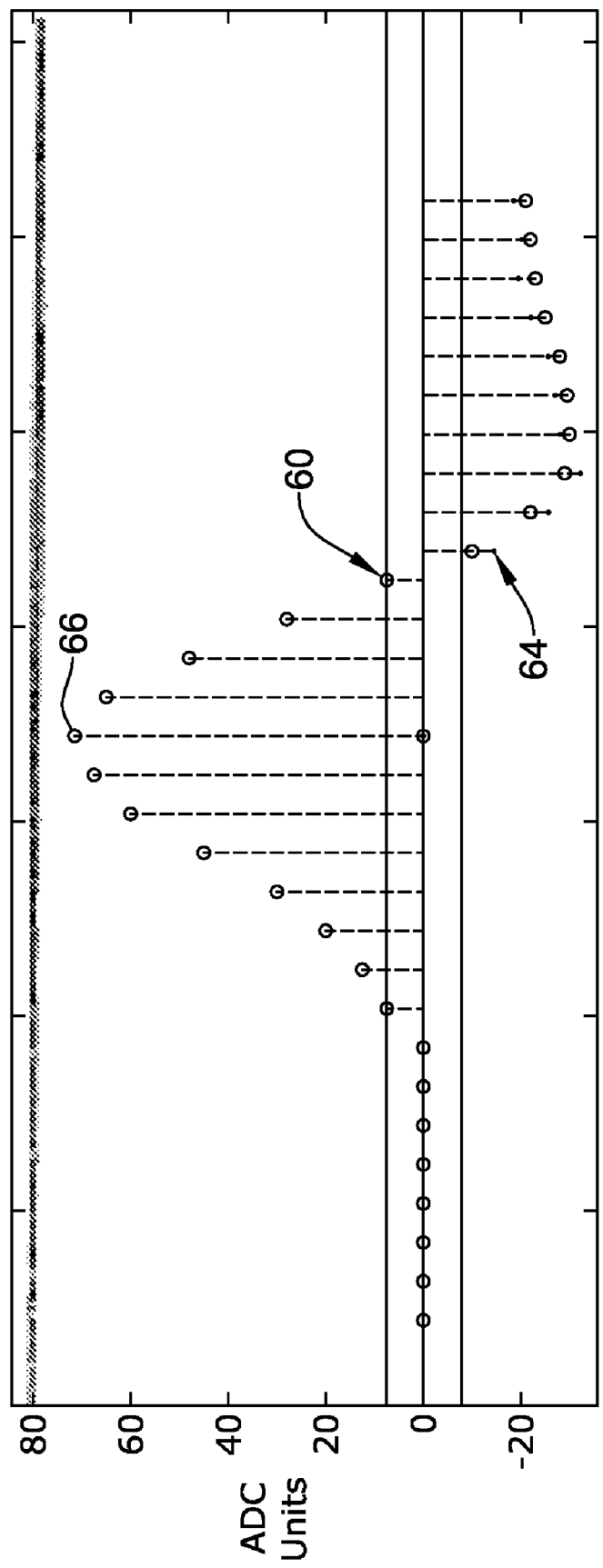
FIG. 6 shows a sensed cardiac complex that correlates well to a sinus template.

FIGS. 5 and 6 illustrate one embodiment of how sensed cardiac complexes compare to a stored sinus template. The sinus templates 60 in FIGS. 5 and 6 are formed as described in detail with reference to FIG. 3. Samples indicating the sinus template 60 are shown as open circle markers. The samples indicating the sampled cardiac complex 62, 64 are shown as cross markers. The examples of FIGS. 5 and 6 make use of thirty samples of an individual cardiac complex; more or less samples may be used with the embodiments illustrated herein.

The sinus template 60 comprises thirty fixed length samples having a peak 66, fifteen samples to the left of the peak 66 and fourteen samples to the right of the peak 66. The comparison technique is initiated by positioning the peak of the sensed cardiac complex 62, 64 at the corresponding peak reference point 66 for the sinus template 60. The detection enhancement operator 42 then places cross markers, for the values representing the sensed cardiac complex 62, 64 at the same fixed length sampling frequency as those circle markers representing the values for the sinus template 60. Following this step, the detection enhancement operator 42 mathematically compares the correlation between the sinus template 60 and the sensed cardiac complex 62, 64. In one embodiment, this comparison evaluates particular attributes that give rise to the difference between the two sets of markers. This correlation technique is repeated for each sensed cardiac complex.

In FIG. 5, the difference between the sensed cardiac complex 62 and the sinus template 60 is considerable. On a CWA scale of zero to 100, where zero means minimal correlation and 100 means a perfect correlation between the compared waveforms, the sensed cardiac complex 62 in FIG. 5 scored a zero. The sensed cardiac complex 62 in FIG. 5 therefore correlated poorly with the sinus template 60. Specifically twenty-one of the thirty cross markers for the sensed cardiac complex 62 did not overlap the circle markers of the sinus template 60. In fact, there is a considerable amount of separation between the sinus template 60 markers and the markers for the sensed cardiac complex 62. Thus, the sensed cardiac complex 62 in FIG. 5 does not resemble a normal sinus cardiac complex.

In contrast, the sensed cardiac complex 64 in FIG. 6 scored over eighty on the same CWA scale as used in FIG. 5. In FIG. 6, only eleven of the thirty cross markers of the sensed cardiac complex 64 did not overlap the circle marker of the sinus template 60. Moreover, the difference in separation between those sinus template 60 markers that did not overlap the markers for the sensed cardiac complex 64 was negligible. As such, the sensed cardiac complex 64 in FIG. 6 correlated strongly with the sinus template 60, and therefore, strongly indicates that the sensed cardiac complex 64 represents a normal sinus complex.

The detection enhancement operator 42 of the present invention is, in a preferred embodiment, capable of running real time CWA, or other morphological analysis, on each beat. For example, each consecutive complex can be compared to the next one (using a dynamic template), or alternatively, each consecutive complex can be compared to the first in the series (using a static template). This ongoing comparison technique can be used to determine in real time if the morphology is mostly unchanging from complex to complex, changing somewhat from complex to complex, or changing significantly from complex to complex—or otherwise generally observing the variability behavior between complexes measured under CWA. Thus, along with the correlation metric derived from running a CWA, a variability metric is gleaned from examining the variability in the CWA from complex to subsequent complex.

Figure 7:
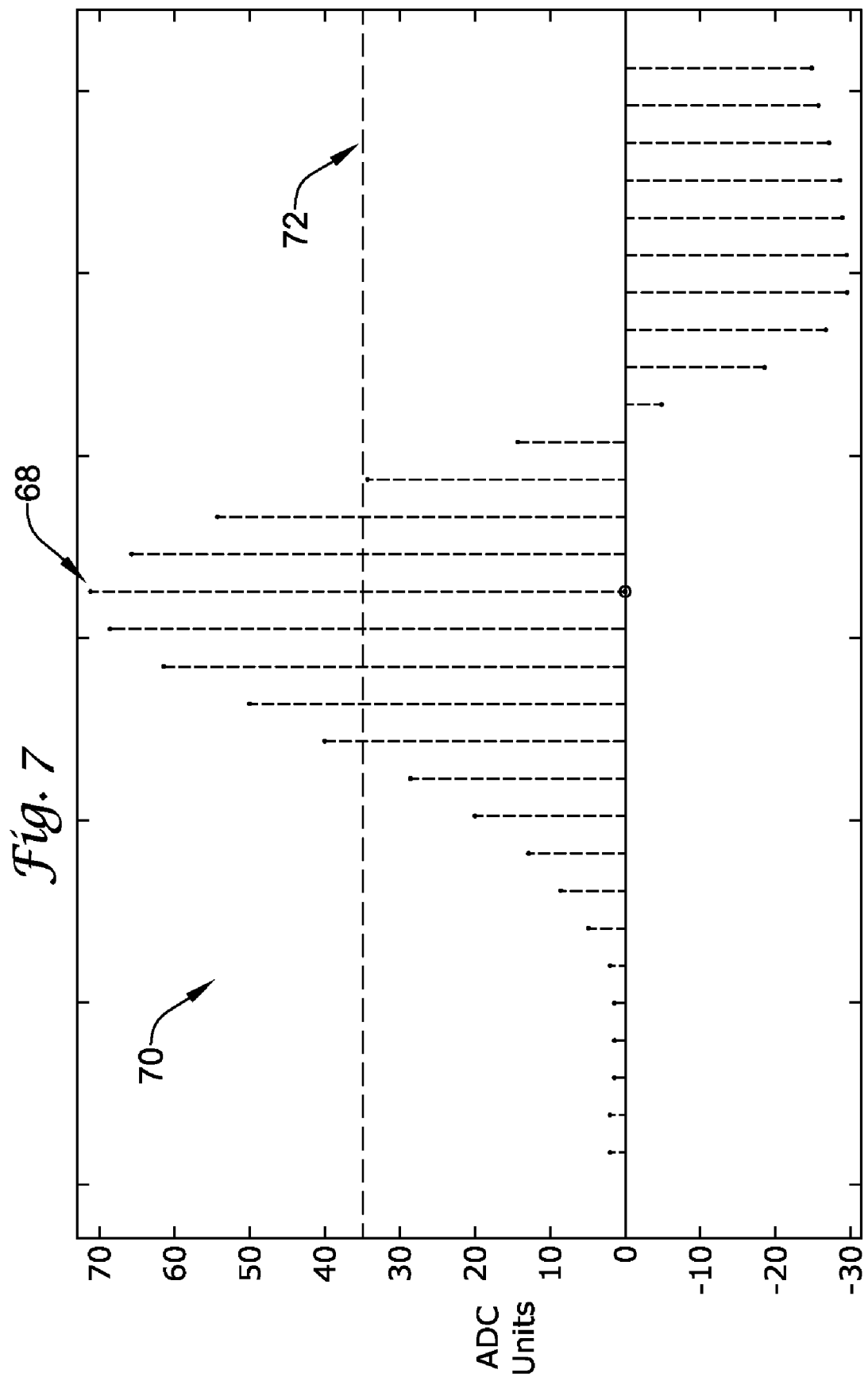
FIG. 7 shows a sensed cardiac complex having a narrow QRS measurement.
Figure 8:
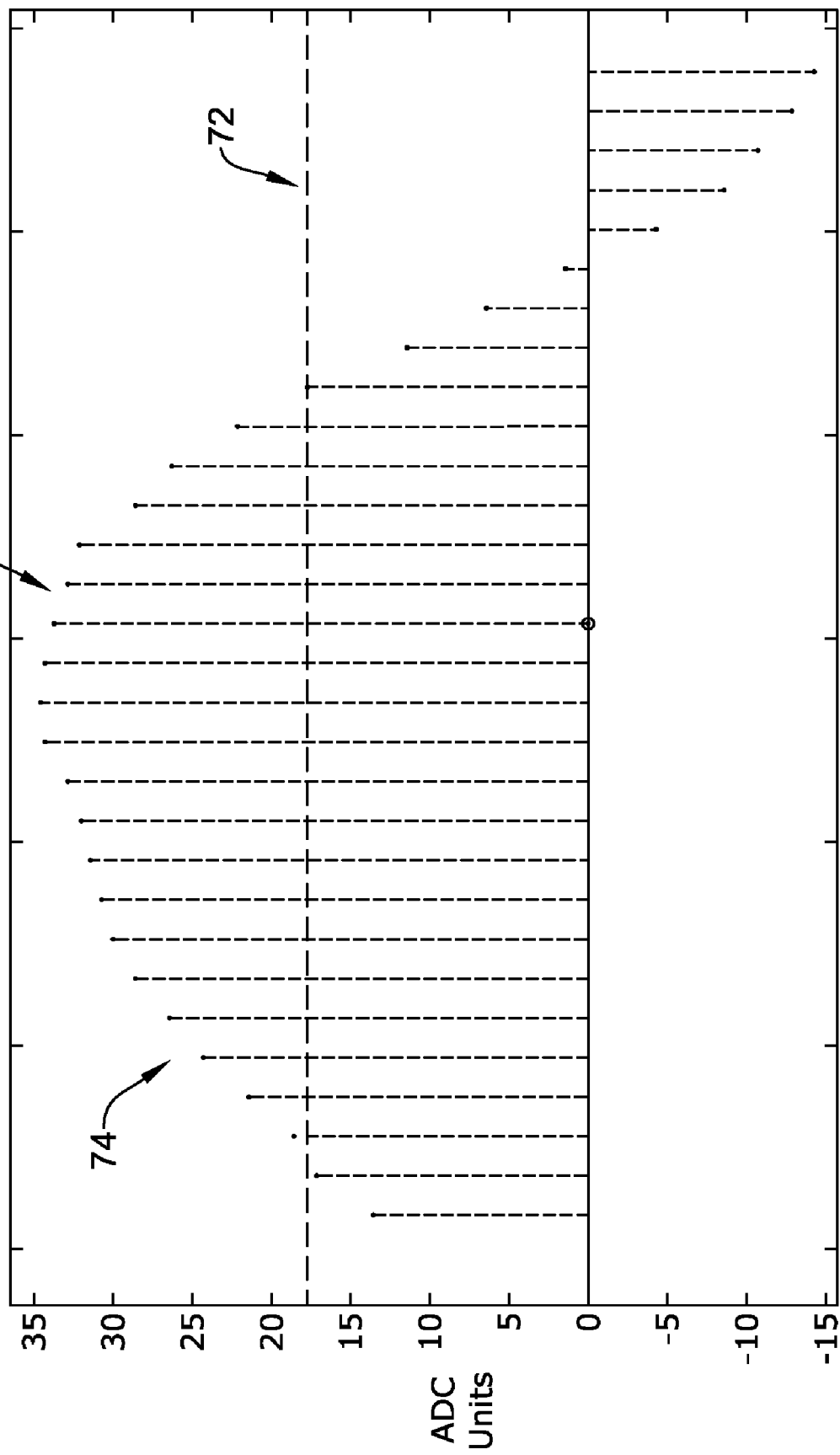
FIG. 8 shows a sensed cardiac complex having a wide QRS measurement.

Another attribute of comparison utilized to distinguish ventricular and supraventricular events is the width of the QRS complex. Although this examination does not compare the QRS width of a complex to a template, it does compare the QRS complex to a predetermined width threshold value. In exemplary embodiments, the QRS width value is determined by making a series of measurements on each individual complex. FIGS. 7 and 8 illustrate how the width value is calculated and shows on two different sensed cardiac complexes whether the complexes are narrow or wide.

In the illustrative example, width value is first calculated by identifying the peak height. In one embodiment, the peak height is measured in ADC units. An ADC is an analog to digital converter, which converts analog signal (in a given range) to its digital equivalent value. For example, an 8 bit ADC operating in the range of +/−10 mV will convert an analog signal of +/−10 mV into +/−127 ADC units. For example, an analog signal of 10 mV is converted to +127 ADC units and an analog signal of −10 mV is converted to −127 ADC units, with linear mapping in-between. With respect to ADC, it may be noted that the use of any one particular format for the digital information (signed/unsigned, ones or twos complement, etc.) is not a requirement of the present invention.

In FIG. 7, the peak height 68 for the sensed cardiac complex 70 is approximately seventy-two ADC units. This would correspond to a 5.6 mV signal (10 mV*72÷128=5.6 mV) going into the ADC. It should be noted that the initially received signal may be filtered and amplified before reaching the ADC.

After calculating the peak height 68, the peak height 68 measurement is divided in half (72÷2=36) to determine the width threshold value 72. The width threshold value 72 for the sensed cardiac complex 70 is approximately thirty-six ADC units, and is indicated by a dotted line. In particular embodiments of the present invention, a narrow cardiac complex is indicated when fewer than approximately thirty-five percent of the sampled complexes lie above the width threshold value 72, and a wide cardiac complex is indicated when more than approximately thirty-five percent of the sampled complexes lie above the width threshold value 72.

According to the above described parameters, the sampled cardiac complex 70 in FIG. 7 is narrow. This figure shows that seven samples out of a total of thirty samples lay above the width threshold value 72. Therefore, approximately 23 percent of the sampled cardiac complex 70 lay above the width threshold value 72. Using the parameters defined, the sampled cardiac complex 70 would be labeled by the detection enhancement operator 42 as a narrow cardiac complex.

The sampled cardiac complex 74 in FIG. 8, in contrast, is wide. FIG. 8 depicts twenty out of a total of thirty samples lay above the width threshold value 72. Therefore, approximately 67 percent of the sampled cardiac complex 74 lies above the width threshold value 72, and as such, would be considered a wide cardiac complex by the detection enhancement operator 42.

In alternative embodiments, the QRS width threshold value is set to a preset value. For example, the width threshold value is set to 100 milliseconds in particular embodiments. Thus, complexes having QRS widths less than 100 milliseconds are considered narrow, whereas QRS widths greater than 100 milliseconds are considered wide. By using an X out of Y filter, a grouping of complexes may be assessed as characteristically wide or narrow. It is then this grouping that may be utilized by the detection enhancement operator 42, alone or in combination, to detect and discriminate between particular arrhythmias. Although 100 milliseconds is used for illustrative purposes, other embodiments of the present invention may use QRS width values between approximately 60 and approximately 175 milliseconds.

Interval rate stability, although not morphological, can also be used as an attribute for comparison. Interval rate stability measures the timing between subsequent complexes. In preferred embodiments, the interval between a first complex and a second complex is within +/−30 milliseconds of the interval between the second complex and a third, subsequent complex. In alternative embodiments the interval rate stability is between +/−5 and +/−85 milliseconds. Interval rate stability is low when deviations in the rate interval fall outside of the predetermined value. Again, a grouping of complexes may be assessed as having a high or low interval rate stability by using an X out of Y filter. The grouping is then analyzed by the detection enhancement operator 42 to discriminate between arrhythmias, the malignancy of the arrhythmias, and the appropriateness of delivery therapy.

A single event that may be used as an attribute for comparison is rate acceleration. Rate acceleration is the abrupt change of cardiac rate (typically considered "abrupt" if occurring within approximately 3-10 cycles) to an elevated and sustained rate of over 120 bpm. This abrupt rate change is characteristic of particular arrhythmias and its appearance may be utilized by the detection enhancement operator 42 of the present invention, alone or in combination, to detect and discriminate between particular arrhythmias.

Utilizing the templates and the comparison techniques described in detail above, the detection enhancement operator 42 of the present invention may direct therapy. In preferred embodiments of the present invention, the detection enhancement operator 42 uses these techniques to direct therapy toward the treatment of ventricular arrhythmias. Examples of ventricular arrhythmias that the detection enhancement operator 42 intends to treat include monomorphic ventricular tachycardia (MVT), polymorphic ventricular tachycardia (PVT) and ventricular fibrillation (VF). These are arrhythmias that are considered malignant and therefore require therapy from an implantable device such as an ICD. Similarly, the detection enhancement operator 42 of the present invention works to preclude the treating of supraventricular arrhythmias. Examples of supraventricular arrhythmias include atrial fibrillation (AF), atrial tachycardia (AT) and sinus tachycardia (ST), where therapy should be avoided; when the intent is to treat a ventricular tachyarrhythmia.

The present invention's ability to discern particular atrial arrhythmias, however, also permits the implementation into devices designed for treating particular atrial arrhythmias, or other arrhythmias that require treatment. For example, the detection architecture of the present invention may be used in devices where it is desirable to discriminate and treat particular supraventricular tachycardias, among others, when desired.

Referring now to Table 1, a comparison chart is depicted representing several comparison methods (outlined in detail below) and the predicted outcomes of these comparisons with various arrhythmias. The arrhythmias in Table 1 include both ventricular arrhythmias requiring therapy and supraventricular arrhythmias where therapy should be withheld. Although Table 1 describes several comparison methods to aid in discriminating between arrhythmias, the present invention is not limited in terms of the scope of Table 1. Other comparison methods may be used, and are contemplated, to populate a similar table for discriminating between arrhythmias.

TABLE 1

|   | AF | AT/ST | MVT | PVT | VF |
|---|---|---|---|---|---|
| A | HIGH | HIGH | LOW | LOW | LOW |
| B | LOW | LOW | LOW | HIGH | HIGH |
| C | HIGH | HIGH | HIGH | LOW | LOW |
| D | LOW | LOW | LOW | HIGH | HIGH |
| E | NARROW | NARROW | WIDE | WIDE | WIDE |
| F | LOW | HIGH | HIGH | LOW | LOW |
| G | NO | YES/NO | YES | YES | YES |

Table 1 uses the following comparison methods and their corresponding definitions:
A = CWA between a sensed complex and a stored sinus template, where HIGH indicates high correlation with a stored sinus template and LOW indicates low correlation with a stored sinus template;
B = Variability in the CWA between a sensed complex and a stored sinus template, where HIGH indicates high variability within a grouping of cardiac complexes and LOW indicates low variability within a grouping of cardiac complexes;
C = CWA between a sensed complex and a template acquired after a triggering event (here, a template representative of a complex with a rate between 170 and 260 bpm), where HIGH indicates high correlation with the template acquired after a triggering event and LOW indicates low correlation with the template acquired after a triggering event;
D = Variability in the CWA between a sensed complex and a template acquired after a triggering event (here, a template representative of a complex with a rate between 170 and 260 bpm), wherein the template is dynamic and continually updated by the previously sensed cardiac complex, where HIGH indicates high variability in the CWA, within a grouping of cardiac complexes when compared to a template acquired after a triggering event and LOW indicates low variability in the CWA within a grouping of cardiac complexes when compared to a template acquired after a triggering event;
E = Comparison to a QRS width threshold value (described in detail above), where WIDE indicates QRS waveforms having greater that 35 percent of their complex laying above the width threshold value and NARROW indicates QRS waveforms having less that 35 percent of their complex laying above the width threshold value;
F = Interval rate stability of +/−30 milliseconds, where YES indicates stability within +/−30 milliseconds and NO indicates stability outside of +/−30 milliseconds; and
G = A rate acceleration event, where YES indicates a rate accelerating event and NO indicates the lack of a rate accelerating event.

For the purposes of the Table 1, a scaled CWA is considered HIGH if it exceeds 50, where the CWA is scaled to be a number between 0-100. Because the CWA is a measure of correlation, in terms of raw data the CWA could potentially have a score between −1 and +1. For Table 1, the scaled CWA is scaled such that any negative CWA result is given a zero, while positive CWA (in raw data) values are multiplied by one hundred to yield a range from 0-100 for the scaled CWA. Using this scale, a CWA below 50 would be considered LOW. Any suitable scale may be used, as desired, or, the CWA may be treated directly without scaling.

For some embodiments, the definitions of HIGH and LOW for the CWA may vary from method to method. For example, while for method A the dividing line between HIGH and LOW may be at about 50 (using the scaled CWA where negative coefficients are zeroed and positive coefficients are multiplied by 100), method D may look for stronger beat-to-beat similarity and set the dividing line at about 70.

By extrapolating the observations in Table 1, it is observed that certain comparison methods may be used to discriminate treatable arrhythmias from arrhythmias where therapy should be withheld. This discrimination process can be accomplished using a single comparison method, or using multiple comparison methods.

The use of a single comparison method to discriminate between all the treatable arrhythmias and those arrhythmias where therapy should be withheld is illustrated using comparison method A. If when running comparison method A the correlation was low, as denoted as LOW in the table, then this result would indicate that the cardiac complex did not correlate with the stored sinus template and that the arrhythmia resembled either MVT, PVT, or VF. In contrast, a score of HIGH in this comparison method indicates an arrhythmia that correlated highly with the stored sinus template, and is indicative of AF, AT and ST in the table. Thus, by running comparison method A alone and receiving a score, the detection enhancement operator 12 of the present invention would allow the delivery or withholding of therapy, depending on the device requirements. The other comparison method that discriminates all the arrhythmias indicating therapy from arrhythmias where therapy should be withheld is comparison method E. In particular, a WIDE score in comparison method E would indicate the delivery of therapy for MVT, PVT and VF arrhythmias and not for AF, AT and ST.

Alternatively, some comparison methods alone can only distinguish particular arrhythmias, and not all the arrhythmias which indicate either therapy is required (i.e., PVT and VF, but silent on MVT) or therapy should be withheld (i.e., AT and AF, but silent on ST). An example of this phenomenon is illustrated by comparison method B. If a HIGH score resulted when running comparison method B, this HIGH score only distinguishes PVT and VF arrhythmias from the other arrhythmias. A HIGH score does not discriminate all of the treatable arrhythmias from the not-treated arrhythmias. Specifically, the treatable arrhythmia MVT scores LOW in comparison method B. A LOW score is also indicative of AF, AT and ST. Thus, alone, comparison method B cannot discriminate all treatable arrhythmias from arrhythmias where therapy should be withheld. The other comparison methods that discriminates certain arrhythmias indicating therapy from arrhythmias where therapy should be withheld are comparison methods C, D and F. These comparison methods similarly only discriminate PVT and VF arrhythmias from the other arrhythmias when used singly. Although these comparison methods may not seem ideal in some circumstances because they do not discriminate all of the treatable arrhythmias, in particular situations, it may make good clinical sense to detect and treat only the most discordant scores.

Certain arrhythmias in Table 1 are strongly indicated when processed through certain comparison methods. These results are unambiguous even when sensed by transvenous lead systems. An example of this phenomenon is the strong indications observed in PVT and VF arrhythmias when running comparison method A. Specifically, a sensed PVT or VF arrhythmic complex will almost always correlate poorly (score as LOW) when compared to a stored sinus template. The ambiguity in this comparison is extremely low with these arrhythmias. Thus, scoring a LOW in comparison method A lends itself to a strong indication for these two particular arrhythmias.

Table 2 shows which of the illustrative comparison methods tease out particular arrhythmias with little to no ambiguity, or alternatively, show a strong indication for the particular arrhythmia.

TABLE 2

|   | AF | AT/ST | MVT | PVT | VF |
|---|---|---|---|---|---|
| A | — | — | — | LOW | LOW |
| B | — | LOW | LOW | HIGH | HIGH |
| C | — | — | — | LOW | LOW |
| D | — | LOW | LOW | HIGH | HIGH |
| E | — | — | — | — | — |
| F | — | — | — | LOW | LOW |
| G | — | —/NO | — | — | — |

Certain entries in Table 1 are influenced by some ambiguity. Because Table 1 was tabulated from data observed by transvenous lead systems, these systems cannot always unambiguously discern vector information that distinguishes attributes specific to particular arrhythmias. The reason for this is that transvenous electrode systems are optimized for local information sensing, their optimization comes at the expense of far field and vector information sensing. This relative lack of far field and vector information sensing translates to relatively frequent ambiguous sensing with certain arrhythmias, such as an atrial fibrillation that is conducted rapidly to the ventricles.

The ambiguity of certain arrhythmias can be high in particular comparison methods. Table 3 shows which of the illustrative comparison methods tease out particular arrhythmias with high ambiguity and their corresponding estimate of ambiguity percentage for a transvenous approach. Table 3 shows the weak indicators for particular arrhythmias. Again, this ambiguity is primarily the result of the data populating Tables 1-3 being observed from transvenous lead systems.

TABLE 3

|   | AF | AT/ST | MVT | PVT | VF |
|---|---|---|---|---|---|
| A | — | — | LOW (20%) | — | — |
| B | — | — | — | — | — |
| C | — | — | HIGH (20%) | — | — |
| D | — | — | — | — | — |
| E | NARROW (33%) | NARROW (33%) | — | — | — |
| F | — | — | — | — | — |
| G | NO (20%) | — | — | YES (20%) | YES (20%) |

Of note, the ambiguity percentages used in Table 3, and all subsequent Tables, are educated estimations based on published studies and clinical observations. It is believed that these results are suitable for extrapolation to a larger population. However, ambiguities in the Tables exist. For example, it is estimated that about 20% of the population will contraindicate an MVT when using either comparison method A or comparison method C. For some embodiments of the present invention, these ambiguity percentages provide a tool for planning a multi-comparison methodology. By knowing the relative ambiguities of any particular comparison method, the detection enhancement operator may determine particular comparison methods more efficaciously over others when discerning particular arrhythmias.

An example of the ambiguity of certain arrhythmias when using certain comparison methods is illustrated when examining comparison method A. In illustration, in transvenous studies, although a MVT arrhythmia will generally correlate poorly (score as LOW) when compared to a stored sinus template, there is an approximately 20 percent chance that a MVT may demonstrate a high correlation and actually score HIGH using the same comparison method. Thus, the influence of these more ambiguous results is troubling when discriminating between arrhythmias, and ultimately in directing therapy.

To compensate for ambiguities in transvenous lead systems, or to add specificity in determining the applicability of therapy, the comparison methods (A-G) may be layered as one-sided algorithms. Layering comparison methods permits maximum efficiency in decision making by the detection enhancement operator. One-sided algorithms (comparison methods) do not necessarily identify certain arrhythmias, but this regime can identify what types of arrhythmias a sensed complex is not. By cascading and layering one-sided algorithms, the specificity increases and the identity of an arrhythmia may be established with great certainty.

This comparison technique can either be single or dual sided. Specifically, the detection enhancement operator 42 can withhold therapy only based on comparison, can deliver therapy only based on comparison, or can hold or deliver therapy based on comparison. These combinational methods can also be used to make decisions as to diagnostic information collected, either alone or in combination with therapy.

However, two-sided algorithms and the running of multiple comparison methods simultaneously do not necessarily add specificity to the detection enhancement operator. In illustration, if multiple comparison methods were run simultaneously, it is possible for the results of the simultaneous run to be worse than if only one comparison method was used alone. This is possible because one comparison method may introduce ambiguity that does not overlie the second comparison method when the two are run together, thereby increasing the ambiguity in the result. Moreover, if the comparison methods were set up so that one is always deferred to, then there would be no need to run the second comparison method at all.

In preferred embodiments of the present invention, it is beneficial to begin the layering of comparison methods with those that introduce the least ambiguity. Thus, all the subsequently following comparison methods are left only to tease out a small percentage of arrhythmias not identified by the first, or preceding comparison methods. By cascading the appropriate comparison methods, the detection enhancement operator of the present invention may properly discriminate a preponderance of the arrhythmias that may present themselves to an implantable device.

Figure 9:
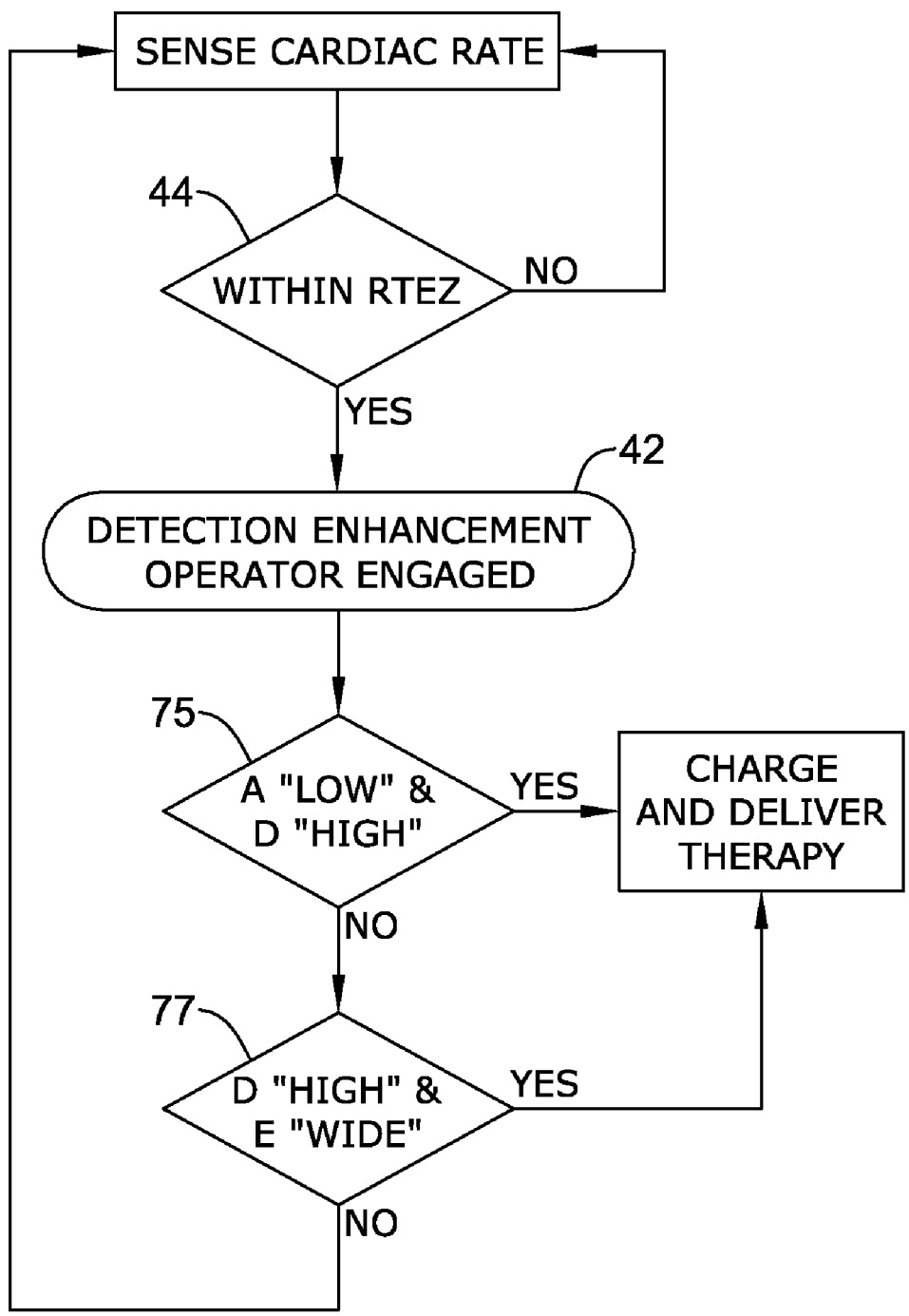
FIG. 9 shows an exemplary embodiment of the present invention using a cascade of comparison methods.

An exemplary model depicting a cascade of comparison methods is illustrated in FIG. 9. The detection enhancement operator 42 shown in FIG. 9 is engaged by having a rate sustained within the rate triggering enhancement zone (RTEZ) 44. If the rate is below this RTEZ 44, the detection enhancement operator 42 is not activated and the system continues to monitor the patient's heart rate. If the rate threshold is met, the detection enhancement operator 42 is engaged and subsequently evaluates the following first layer of questioning 75—does comparison method A result in a LOW score and (a Boolean AND) does comparison method D result in a HIGH score? A "yes" answer to this Boolean query unambiguously identifies arrhythmias PVT and VF. Both PVT and VF demonstrate strong indications for these queries, as illustrated in Table 2. Additionally, because these arrhythmias require therapy, the device would then be directed to deliver a therapeutic shock following this "yes" answer. A "no" answer to this Boolean query, however, would result in the detection enhancement operator 42 asking a second layer question 77.

In the second layer of questioning 77, the detection enhancement operator 42 evaluates the following—does comparison method D result in a HIGH score and (a Boolean AND) does comparison method E result in a WIDE score? A "yes" answer to this Boolean query most likely identifies the arrhythmia MVT. The necessity for asking the second layer question 77 is to remove any ambiguity that a MVT arrhythmia did not uncharacteristically correlate highly in comparison method A when asked in the first layer of questioning 75. If a MVT did correlate highly (as indicated as possible in Table 3) the first layer of questioning 70 could miss this arrhythmia that would require treatment. However, by Boolean ANDing comparison method D with comparison method E, the preponderance of MVT arrhythmias would be detected. More specifically, there would be an extremely low probability that a MVT arrhythmia would correlate highly with a stored sinus template and also have a narrow QRS complex. Thus, a "yes" answer to this Boolean query identifies the arrhythmia MVT and a "no" answer to this Boolean query identifies a supraventricular arrhythmia.

Figure 13:
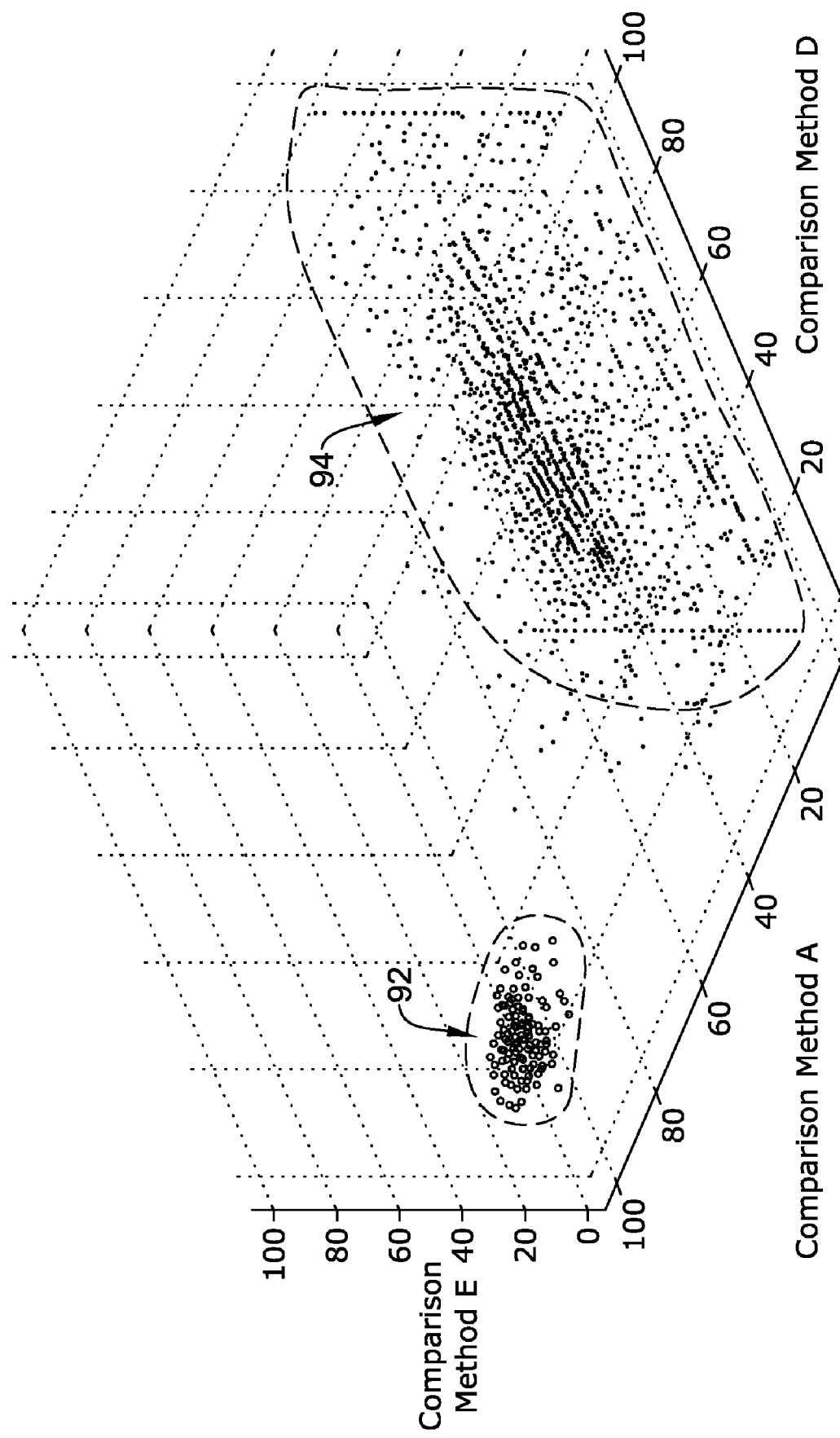
FIG. 13 depicts a graph showing the Boolean results on the sampled electrocardiogram using comparison methods A, D and E.

FIGS. 10-13 illustrate how the cascade described in FIG. 9 functions on a sample electrocardiogram, and further how the detection enhancement operator 42 identifies an arrhythmia in the sample electrocardiogram. Unlike the method described in FIG. 9, however, the graphs in FIGS. 11-13 are the result of the detection enhancement operator 42 being continually on, and not triggered through an RTEZ 44. As such, the graphs will include markers for both normal sinus rhythms as well as rhythms following a triggering event to illustrate the effectiveness of the cascading technique.

Figure 10:
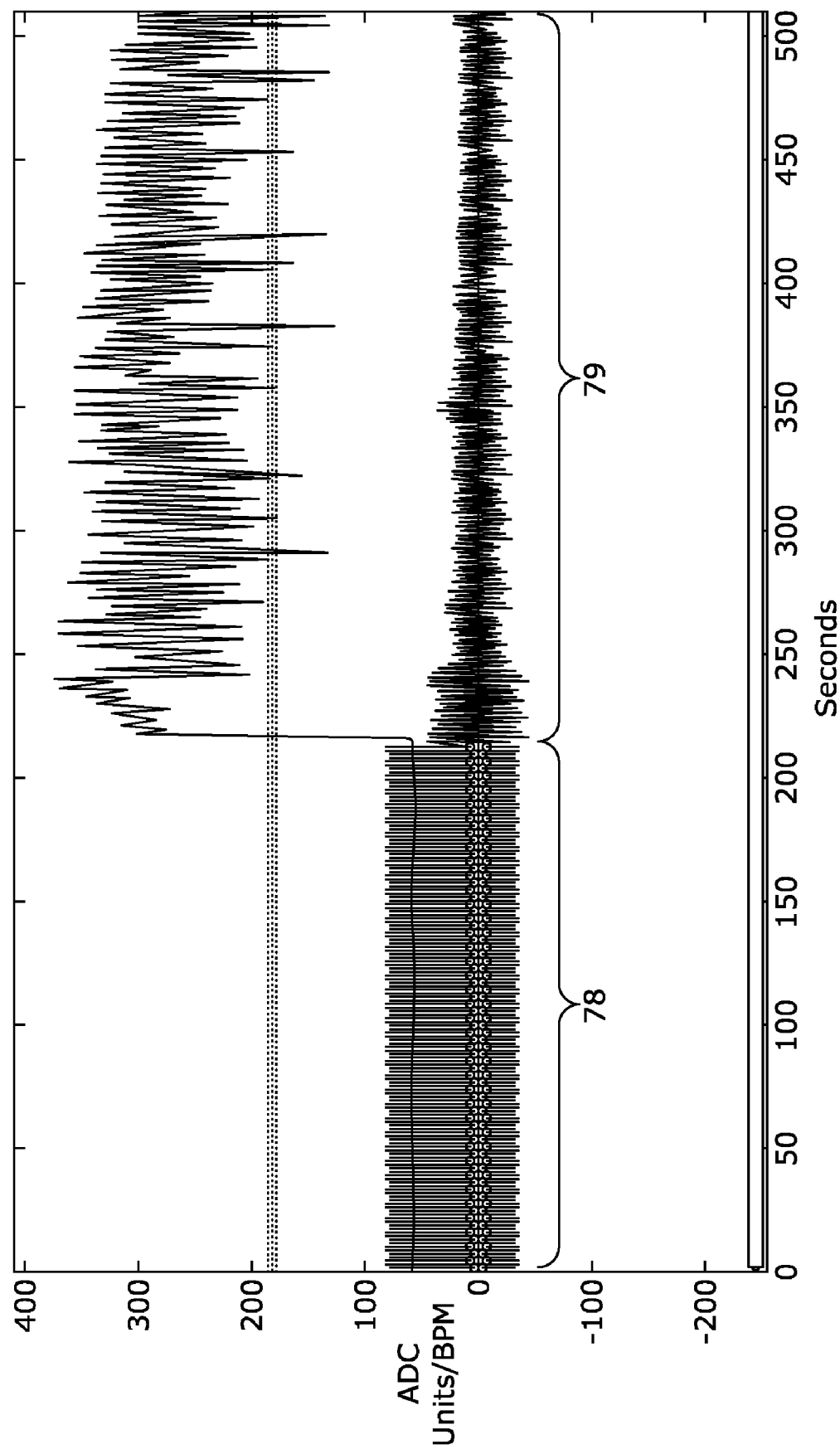
FIG. 10 depicts a sampled electrocardiogram having a normal sinus segment and a segment having an arrhythmic event.

FIG. 10 is a 500 second sample electrocardiogram having a normal sinus rhythm segment 78 and an arrhythmia segment 79. The rhythm prior to the approximately 215 second mark is indicative of normal sinus. However, following the 215 second mark the rate accelerates abruptly and dramatically.

FIG. 11 depicts graphically the first layer of questioning 75—does comparison method A result in a LOW score and (a Boolean AND) does comparison method D result in a HIGH score? The results of comparison method A are plotted on the y-axis of the graph and the results of comparison method D are plotted on the x-axis. After plotting the results of this question against all of the complexes in the sample electrocardiogram, three distinct regions appear.

The first region 80 in FIG. 11 is indicative of rhythms of supraventricular origin. More specifically, the rhythms in the first region 80 are normal sinus and correspond to those cardiac complexes observed prior to the 215 second mark in the sample electrocardiogram. These rhythms have cardiac complexes that do correlate well with the normal sinus template and would have low variability with a template formed from a preceding complex. As such, these complexes populate the top left hand corner of the graph.

The rhythms populating the second region 82 and the third region 84 of the graph are ventricular in origin and indicative of ventricular arrhythmias. The cardiac complexes comprising the rhythm observed following the 215 second mark include both MVT and PVT rhythms. MVTs generally correlate poorly with a normal sinus template; however, these rhythms do not have considerable variability between complexes. As such, these rhythms have a low variability score (comparison method D) and are found in the second region 82 of the graph. In contrast, although PVTs also correlate poorly with a normal sinus template, they also have considerable variability between succeeding complexes. Thus, these rhythms have a high variability score and would be found populating the third region 84 of the graph.

For cardiac complexes that resulted in a clear "yes" answer to this Boolean query (those complexes populating the third region 84 and some portions of the second region 82), the detection enhancement operator 42 unambiguously identifies the arrhythmias as PVT or VF. Additionally, because these arrhythmias require therapy, the device would then be directed to deliver a therapeutic shock following this "yes" answer. In contrast, a clear "no" answer to this Boolean query (those complexes populating the first region 80 of the graph) would direct the detection enhancement operator 42 to withhold therapy based on the comparisons. Finally, an indecisive or weak "no" answer to this Boolean query (those complexes populating some portions of the second region 82) would result in the detection enhancement operator 12 asking the second layer question 77.

FIG. 12 depicts graphically the second layer of questioning 77—does comparison method D result in a HIGH score and (a Boolean AND) does comparison method E result in a WIDE score? Again, three distinct regions arise out of the graph in FIG. 12. The first region 86 comprises those complexes having a narrow QRS complex and possessing a low variability between succeeding cardiac complexes. Rhythms indicative of these characteristics are supraventricular in origin and generally correspond to normal sinus. In contrast, ventricular originating rhythms (MVT, PVT and VF) possess a wide QRS complex. In addition to possessing a wide QRS, MVTs also have a low variability between successive complexes, and therefore, populate the second region 88 in the graph. Similarly, the PVTs and VFs demonstrate a high variability between successive complexes and therefore populate the third region 90 in the graph.

A three dimensional representation of both the first and the second layer of questioning 75, 77 is depicted in FIG. 13. Comparison methods A, D and E align the three axes of the graph. When the detection enhancement operator 42 evaluates the first and second layer of questioning 75, 77 on the sample electrocardiogram, a distinct pattern arises. Specifically, the supraventricular cardiac complexes 92 (normal sinus rhythms) clearly segregate themselves from the remaining ventricular originating complexes 94. Moreover, as indicated above, the result of the first and second layer of questioning 75, 77 enables the detection enhancement operator 42 to withhold therapy based on the comparisons, deliver therapy based on the comparisons, or hold or deliver therapy based on the comparisons. In the present example, the detection enhancement operator 42 would withhold therapy on those complexes in the supraventricular region 92 of graph and deliver therapy to those complexes in the ventricular region 94.

FIGS. 14 through 19 depict other illustrative detection enhancement embodiments of the present invention using cascading and the Boolean ANDing of comparison methods. Moreover, FIGS. 16, 17, 18 and 19 show embodiments of the present invention that include a third layer of questioning for enhancing specificity when discriminating between arrhythmias, and ultimately for directing therapy.

Figure 14:
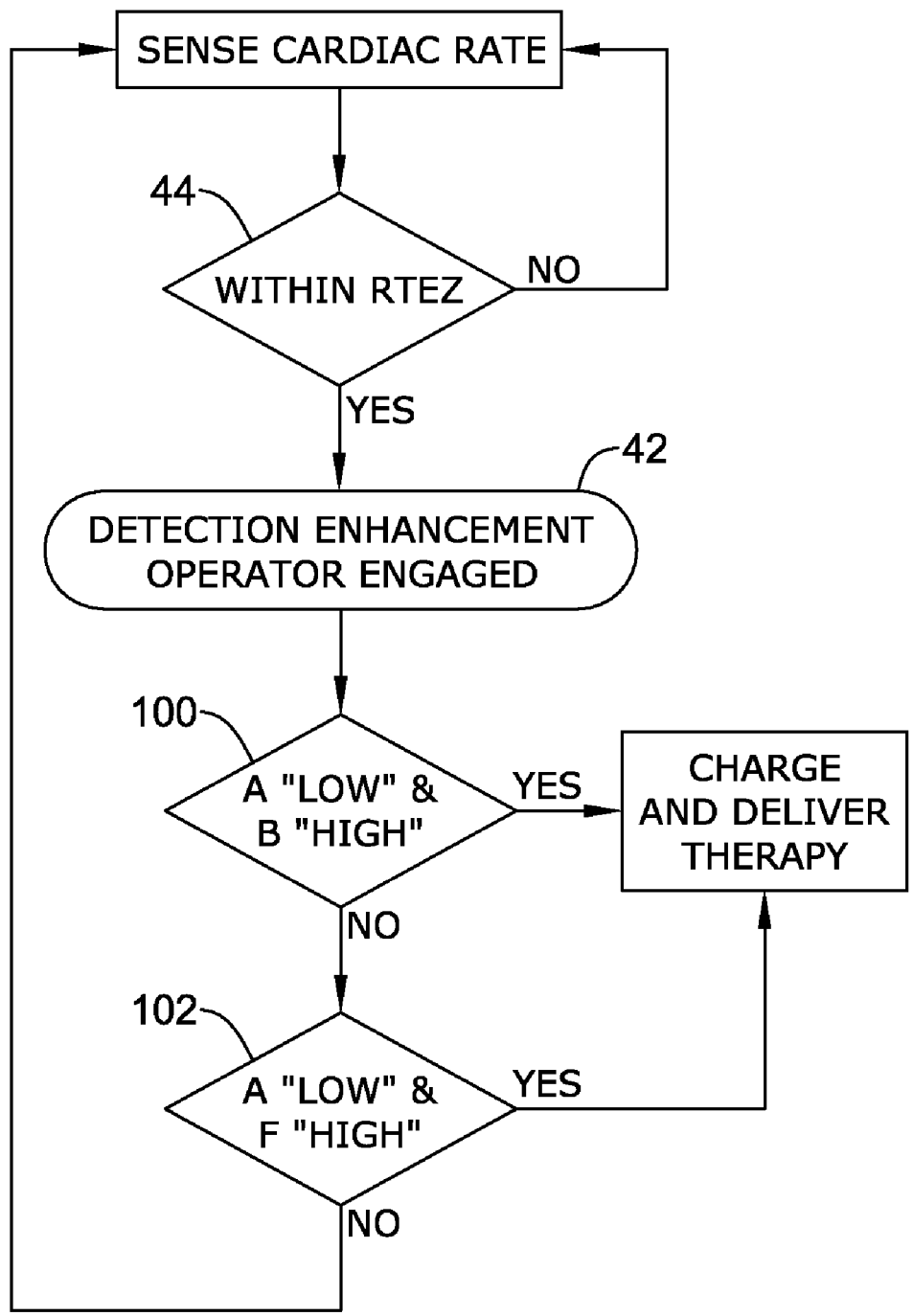
FIG. 14 through FIG. 19 illustrates other detection enhancement operator embodiments of the present invention using cascading and the Boolean ANDing of comparison methods.

Turning to FIG. 14, the illustrative method senses the cardiac rate and determines whether the cardiac rate is within the RTEZ 44. If so, the detection enhancement operator 42 is engaged, and a first layer of determination is whether A=LOW and B=HIGH, as shown at 100. If so, the system charges and delivers therapy. If not, the detection enhancement operator 42 makes a second layer determination of whether A=LOW and F=HIGH, as shown at 102. Again, if so, the system charges and delivers therapy; if both queries 100, 102 yield no results, the system goes back to sensing the cardiac rate.

Figure 15:
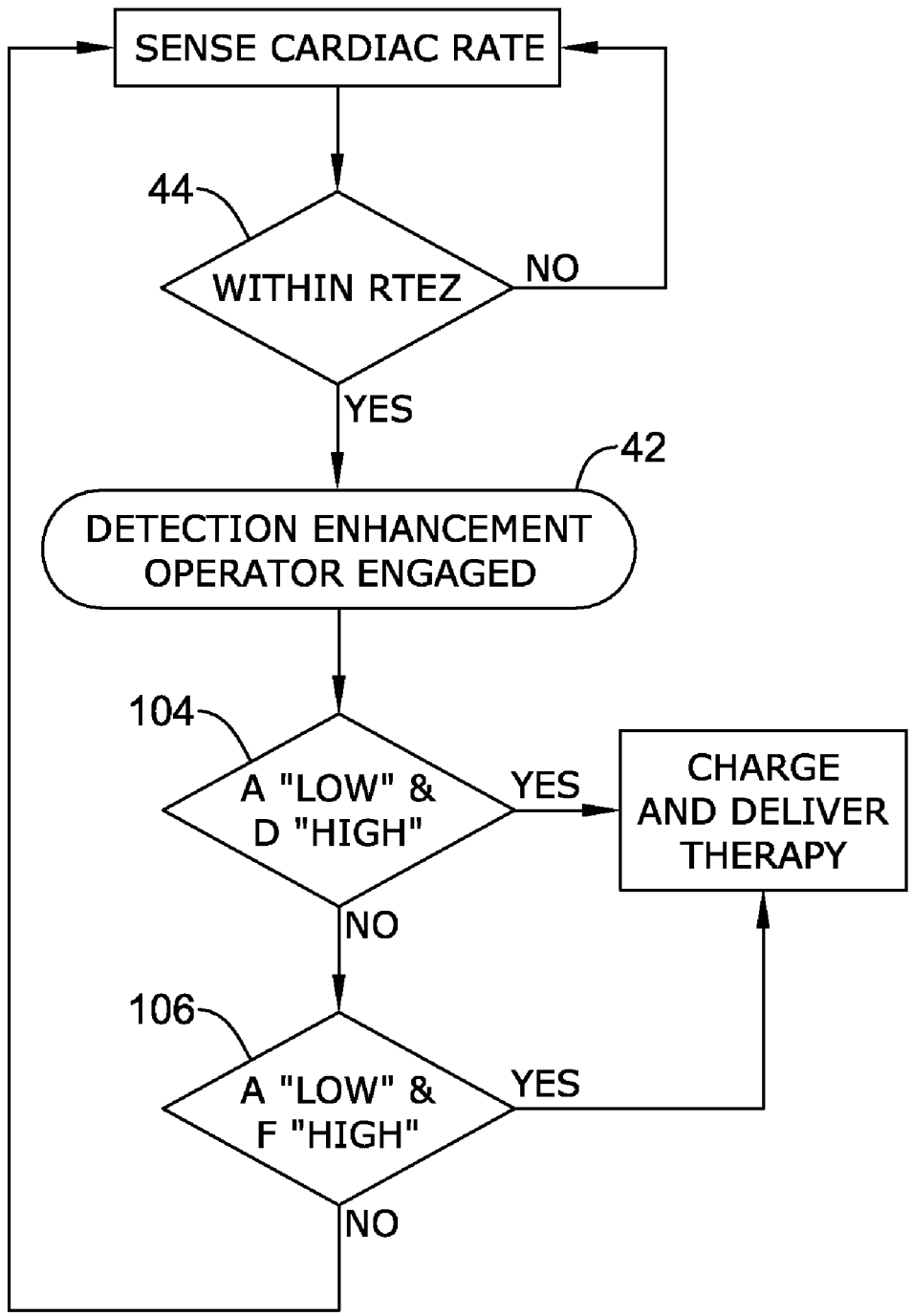

Turning to FIG. 15, the illustrative method senses the cardiac rate and determines whether the cardiac rate is within the RTEZ 44. If so, the detection enhancement operator 42 is engaged, and a first layer of determination is whether A=LOW and D=HIGH, as shown at 104. If so, therapy is delivered. Otherwise, the detection enhancement operator 42 makes a second layer determination of whether A=LOW and F=HIGH, as shown at 106. If so, therapy is delivered. If both queries 104, 106 fail, the system returns to sensing the cardiac rate.

Figure 16:
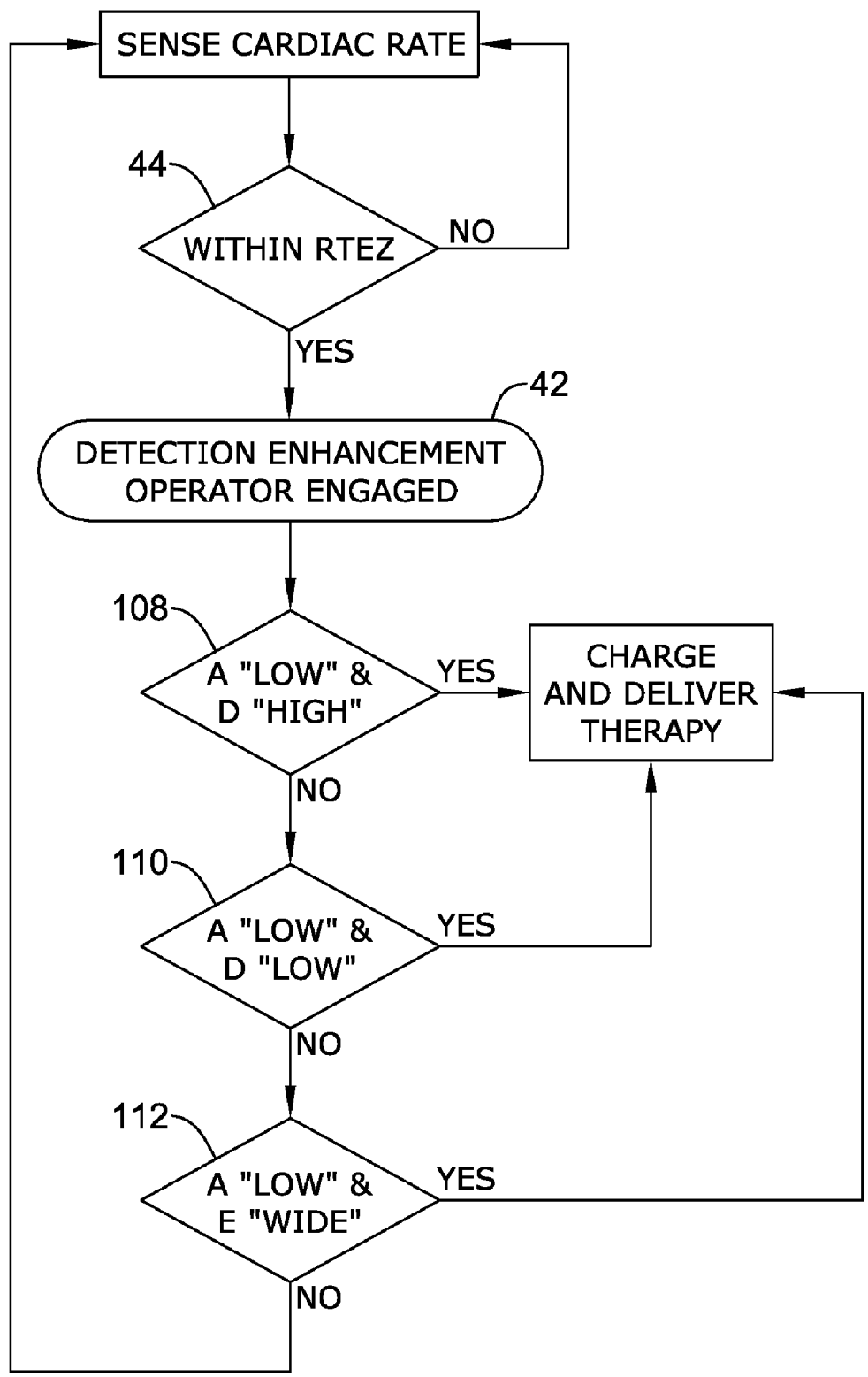

Turning to FIG. 16, the illustrative method senses the cardiac rate and determines whether the cardiac rate is within the RTEZ 44. If so, the detection enhancement operator 42 is engaged, and a first layer of determination is whether A=LOW and D=HIGH, as shown at 108. If so, therapy is delivered. Otherwise, the detection enhancement operator 42 makes a second layer determination of whether A=LOW and D=LOW, as shown at 110. If so, therapy is delivered. Otherwise, the detection enhancement operator 42 makes a third layer determination of whether A=LOW and E=WIDE, as shown at 112. If so, therapy is delivered. If all three queries 108, 110, 112 fail, the system returns to sensing the cardiac rate.

Figure 17:
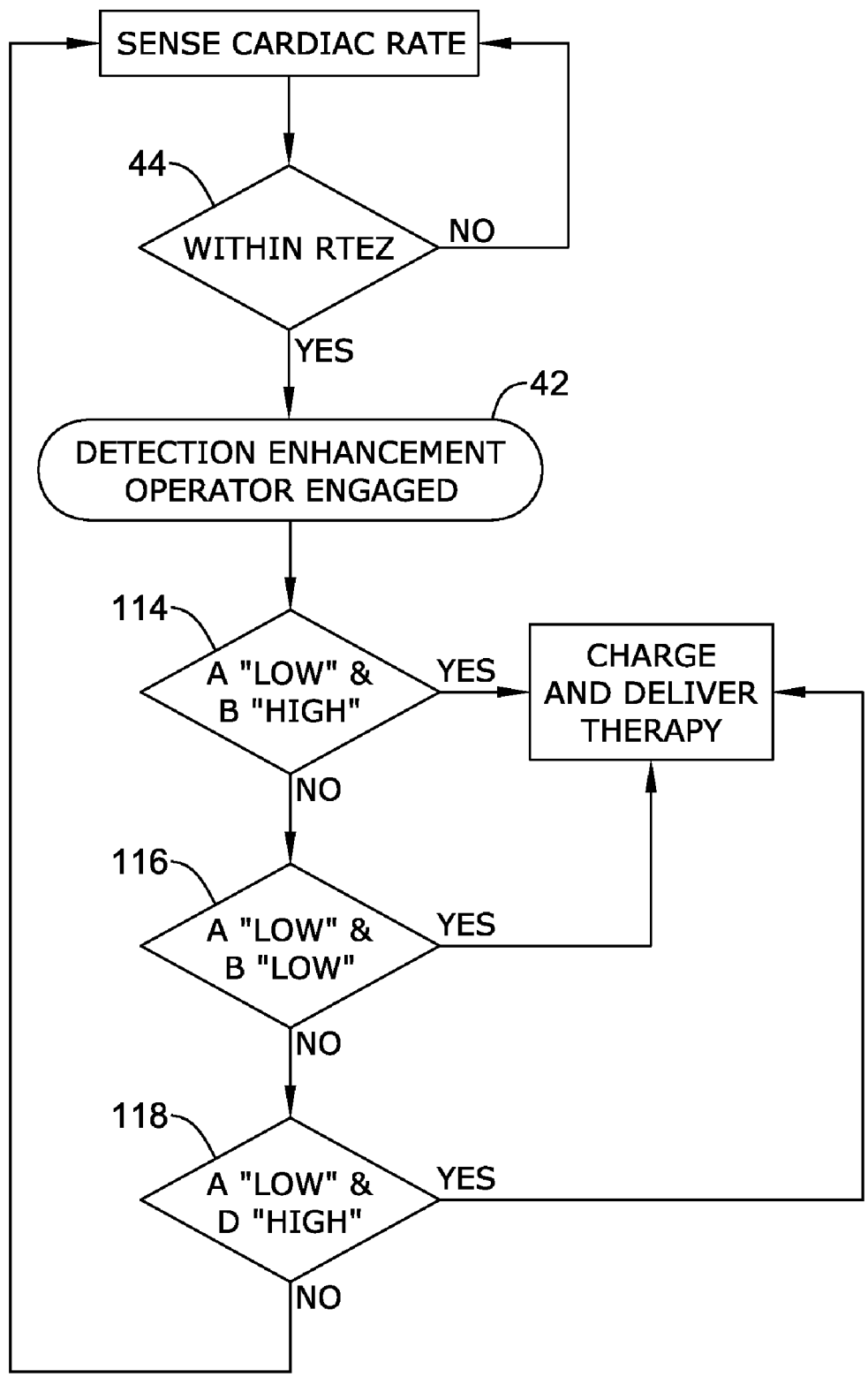

Turning to FIG. 17, the illustrative method senses the cardiac rate and determines whether the cardiac rate is within the RTEZ 44. If so, the detection enhancement operator 42 is engaged, and a first layer of determination is whether A=LOW and B=HIGH, as shown at 114. If so, therapy is delivered. Otherwise, the detection enhancement operator 42 makes a second layer determination of whether A=LOW and B=LOW, as shown at 116. If so, therapy is delivered. Otherwise, the detection enhancement operator 42 makes a third layer determination of whether A=LOW and D=HIGH, as shown at 118. If so, therapy is delivered. If all three queries 114, 116, 118 fail, the system returns to sensing the cardiac rate.

Figure 18:
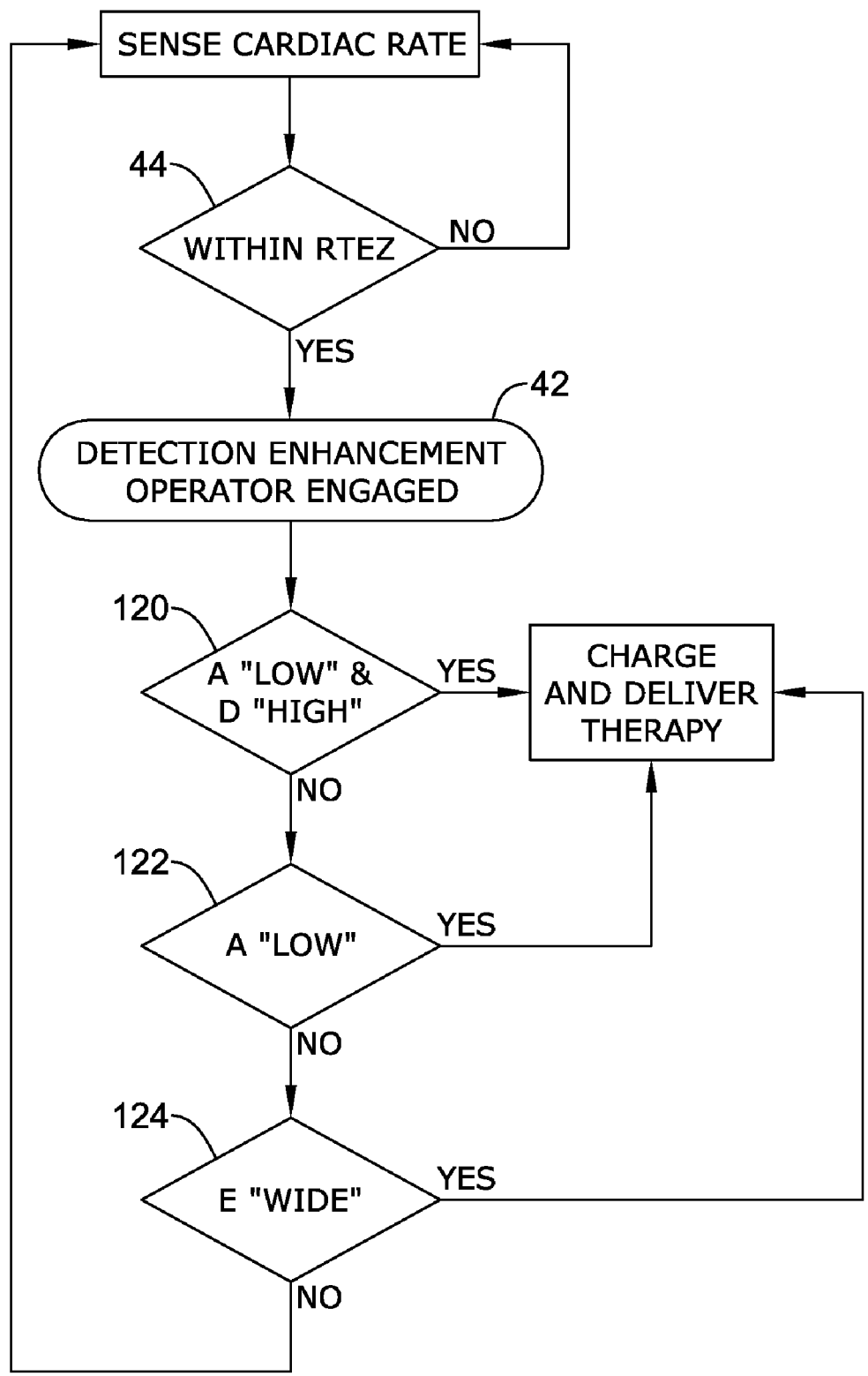

Turning now to FIG. 18, the illustrative method senses the cardiac rate and determines whether the cardiac rate is within the RTEZ 44. If so, the detection enhancement operator 42 is engaged and makes a first layer determination of whether A=LOW and D=HIGH, as shown at 120. If so, therapy is delivered. Otherwise, the detection enhancement operator 42 makes a second layer determination of whether A=LOW, as shown at 122. If so, therapy is delivered. Otherwise, the detection enhancement operator 42 makes a further third layer determination of whether E=WIDE, as shown at 124. If so, therapy is delivered. If all three queries 120, 122, 124 fail, the system returns to sensing the cardiac rate.

Figure 19:
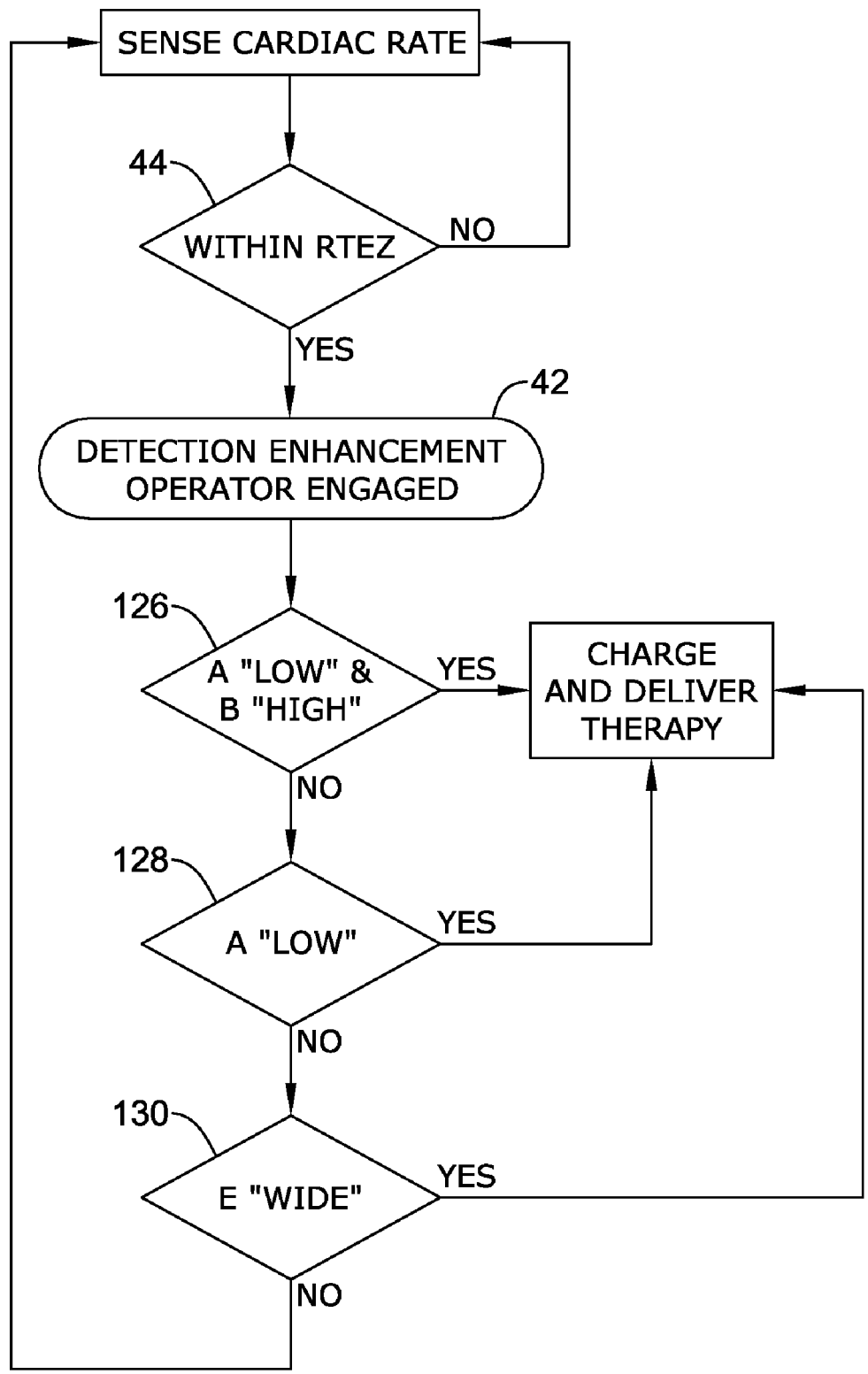

Turning now to FIG. 19, the illustrative method senses the cardiac rate and determines whether the cardiac rate is within the RTEZ 44. If so, the detection enhancement operator 42 is engaged and makes a first layer determination of whether A=LOW and B=HIGH, as shown at 126. If so, then therapy is delivered. Otherwise, the detection enhancement operator 42 makes a second layer determination of whether A=LOW, as shown at 128. If so, therapy is delivered. Otherwise, the detection enhancement operator 42 makes a further third layer determination of whether E=WIDE, as shown at 130. If so, therapy is delivered. If all three queries 126, 128, 130 fail, the system returns to sensing the cardiac rate.

FIG. 20 through FIG. 29 show additional illustrative detection enhancement embodiments using cascading non-Boolean comparison methods.

Figure 20:
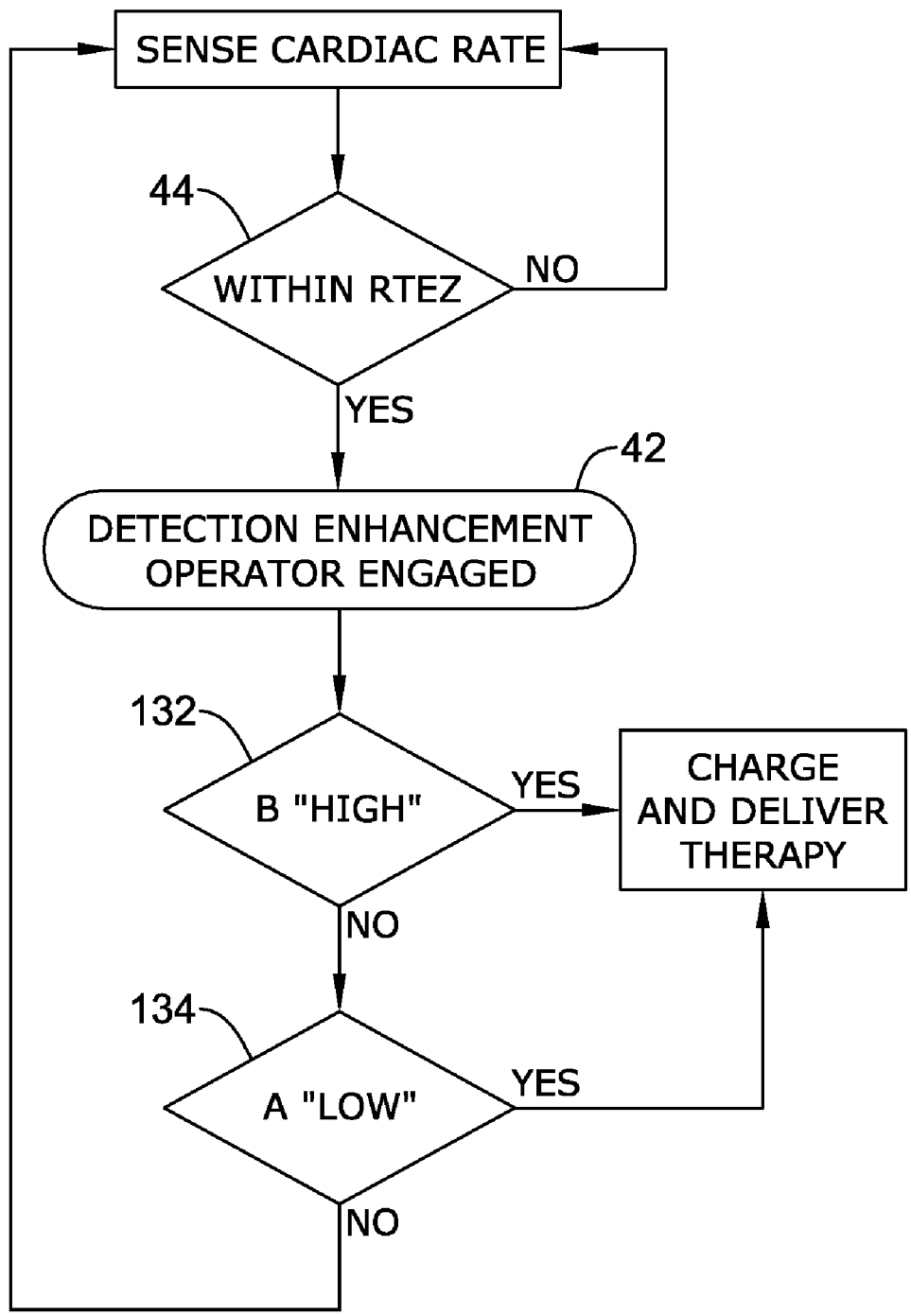
FIG. 20 through FIG. 29 show additional detection enhancement operator embodiments using cascading non-Boolean comparison methods.

Turning now to FIG. 20, the illustrative method senses the cardiac rate and determines whether the cardiac rate is within the RTEZ 44. If so, the detection enhancement operator 42 is engaged and makes a first layer determination of whether B=HIGH, as shown at 132. If so, therapy is delivered. Otherwise, the detection enhancement operator 42 makes a second layer determination of whether A=LOW, as shown at 134. If so, therapy is delivered. If both queries 132, 134 fail, the system returns to sensing the cardiac rate.

Figure 21:
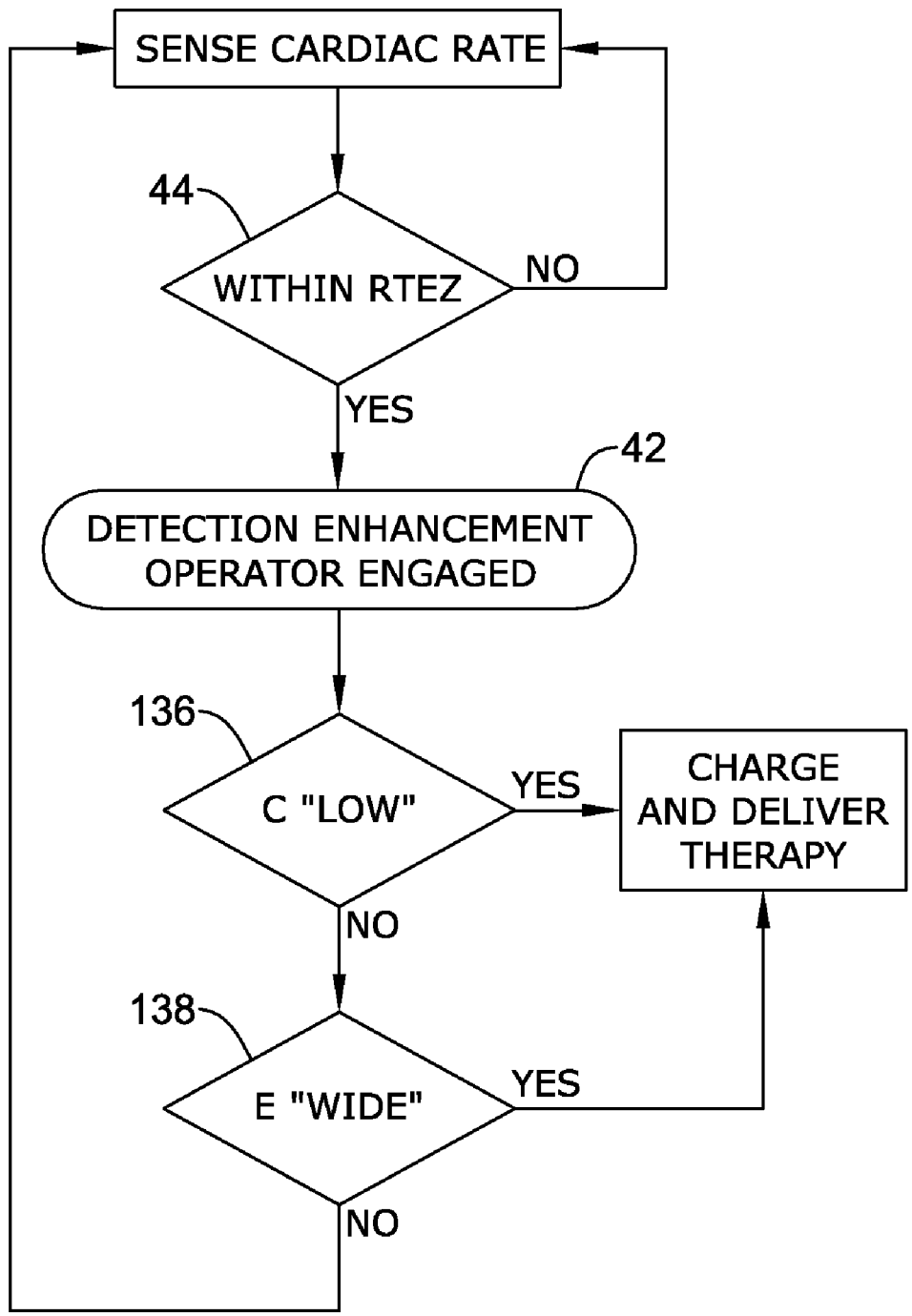

Turning now to FIG. 21, the illustrative method senses the cardiac rate and determines whether the cardiac rate is within the RTEZ 44. If so, the detection enhancement operator 42 is engaged and makes a first layer determination of whether C=LOW, as shown at 136. If so, therapy is delivered. Otherwise, the detection enhancement operator 42 makes a second layer determination of whether E=WIDE, as shown at 138. If so, therapy is delivered. If both queries 136, 138 fail, the system returns to sensing the cardiac rate.

Figure 22:
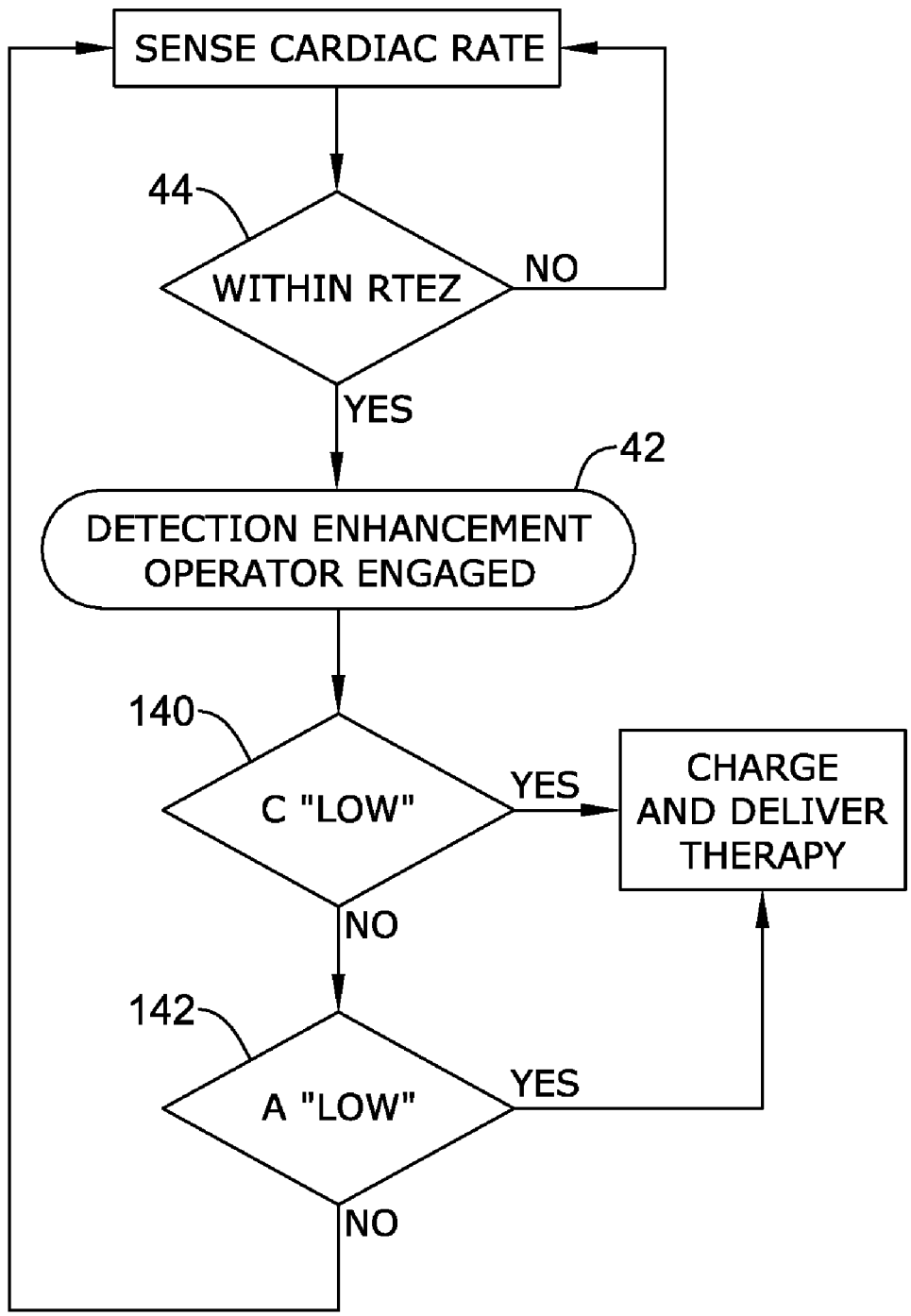

Turning now to FIG. 22, the illustrative method senses the cardiac rate and determines whether the cardiac rate is within the RTEZ 44. If so, the detection enhancement operator 42 is engaged and makes a first layer determination of whether C=LOW, as shown at 140. If so, therapy is delivered. Otherwise, the detection enhancement operator 42 makes a second layer determination of whether A=LOW, as shown at 142. If so, therapy is delivered. If both queries 140, 142 fail, the system returns to sensing the cardiac rate.

Figure 23:
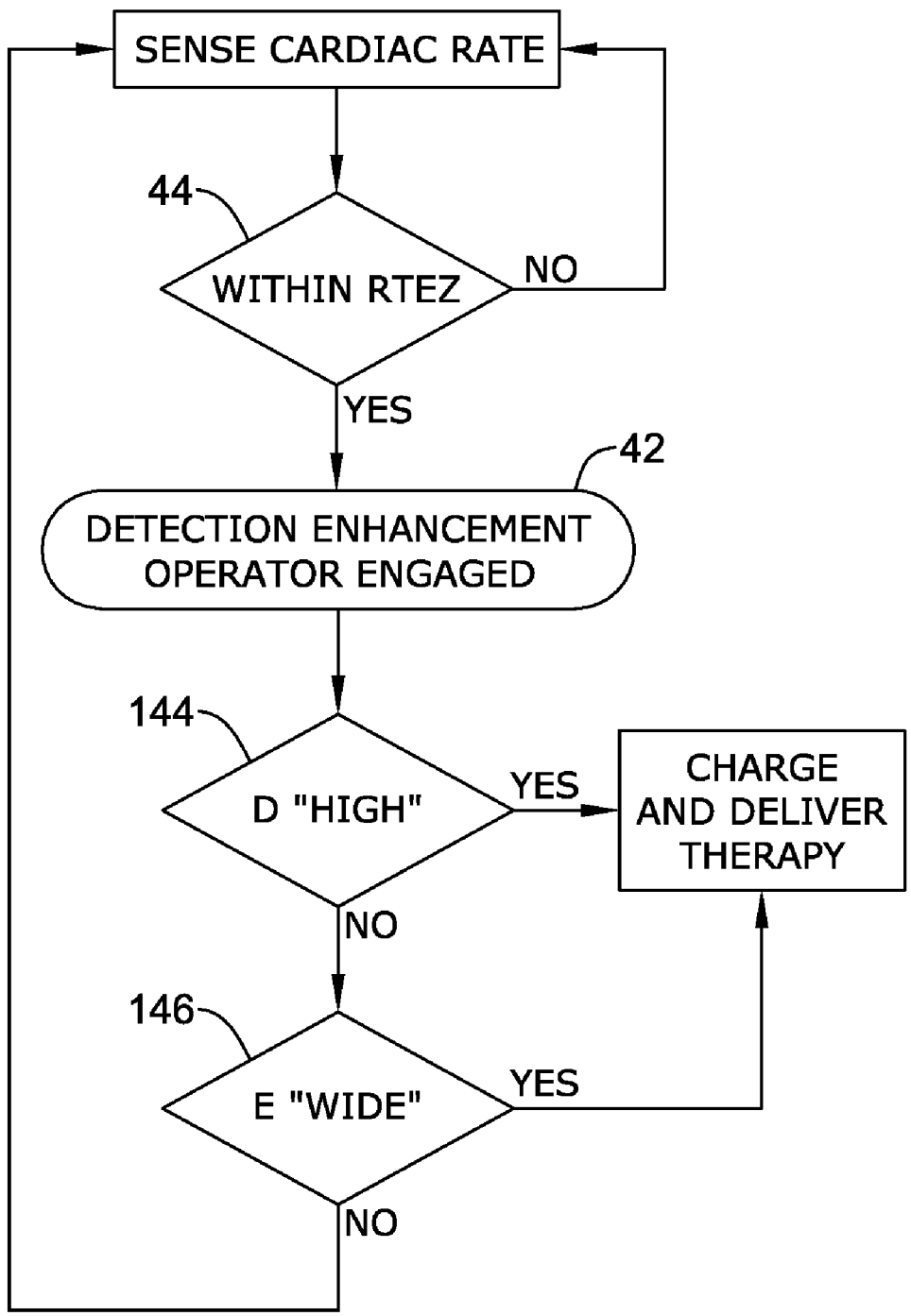

Turning now to FIG. 23, the illustrative method senses the cardiac rate and determines whether the cardiac rate is within the RTEZ 44. If so, the detection enhancement operator 42 is engaged and makes a first layer determination of whether D=HIGH, as shown at 144. If so, therapy is delivered. Otherwise, the detection enhancement operator 42 makes a second layer determination of whether E=WIDE, as shown at 146. If so, therapy is delivered. If both queries 144, 146 fail, the system returns to sensing the cardiac rate.

Figure 24:
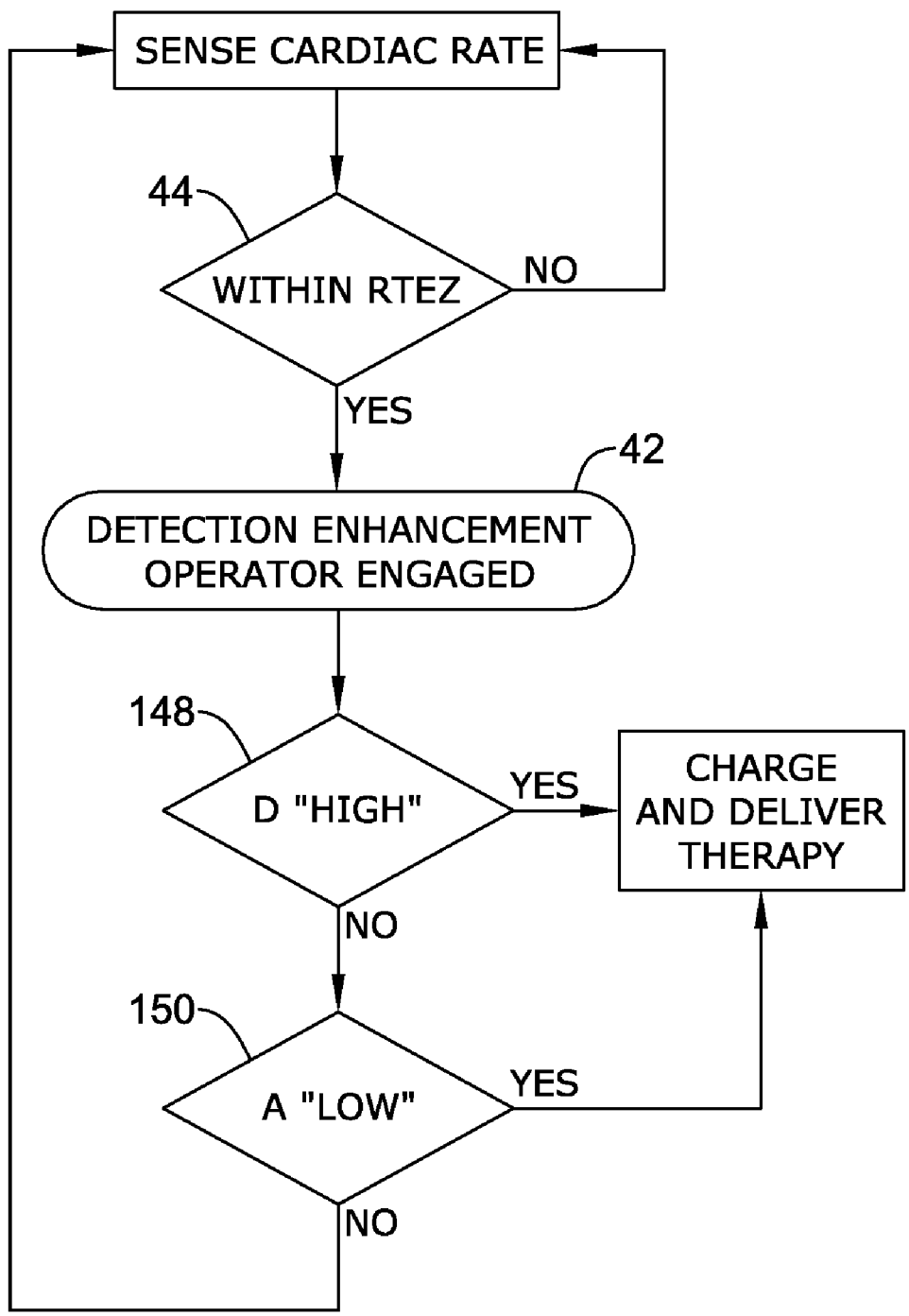

Turning now to FIG. 24, the illustrative method senses the cardiac rate and determines whether the cardiac rate is within the RTEZ 44. If so, the detection enhancement operator 42 is engaged and makes a first layer determination of whether D=HIGH, as shown at 148. If so, therapy is delivered. Otherwise, the detection enhancement operator 42 makes a second layer determination of whether A=LOW, as shown at 150. If so, therapy is delivered. If both queries 148, 150 fail, the system returns to sensing the cardiac rate.

Figure 25:
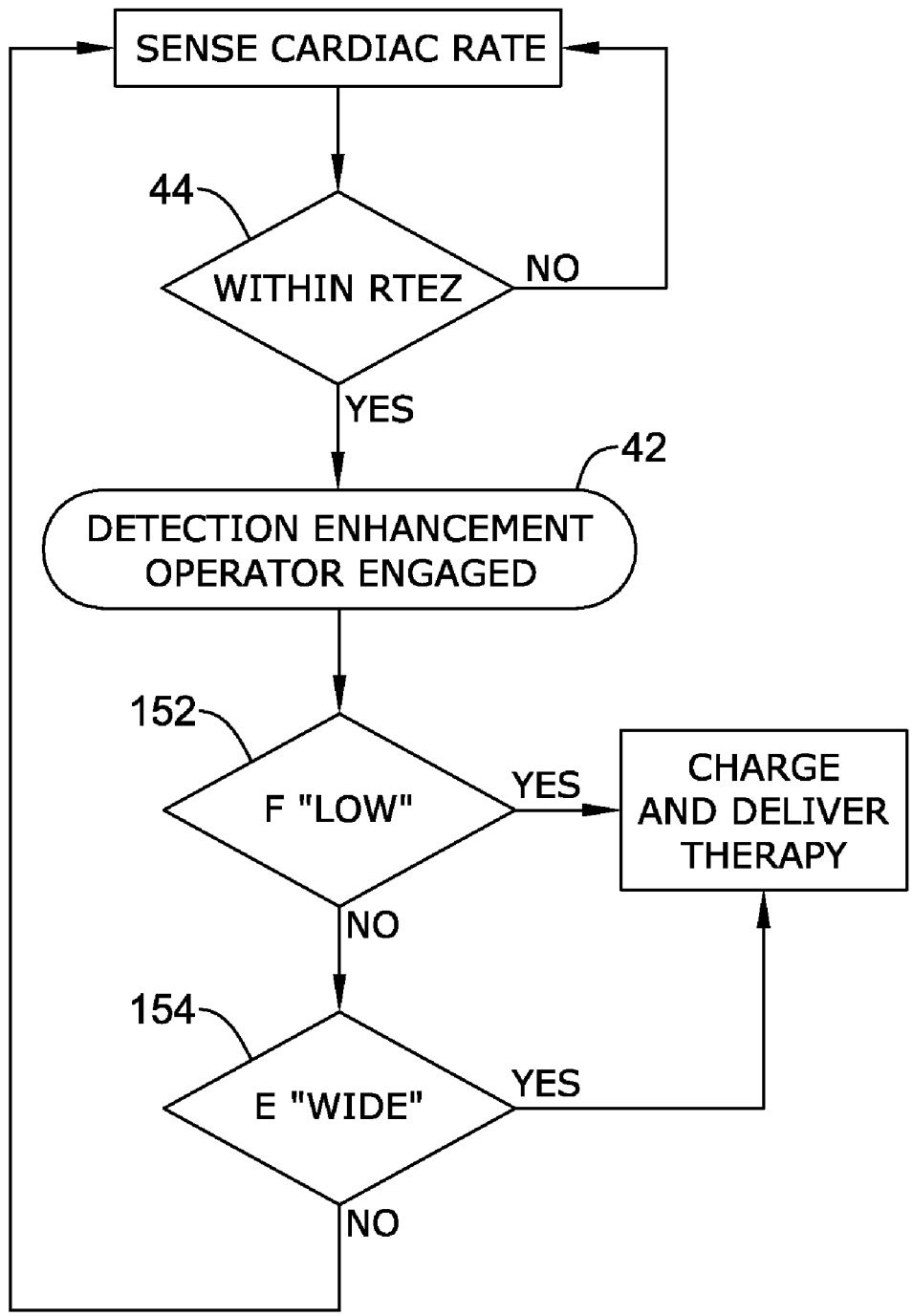

Turning now to FIG. 25, the illustrative method senses the cardiac rate and determines whether the cardiac rate is within the RTEZ 44. If so, the detection enhancement operator 42 is engaged and makes a first layer determination of whether F=LOW, as shown at 152. If so, therapy is delivered. Otherwise, the detection enhancement operator 42 makes a second layer determination of whether E=WIDE, as shown at 154. If so, therapy is delivered. If both queries 152, 154 fail, the system returns to sensing the cardiac rate.

Figure 26:
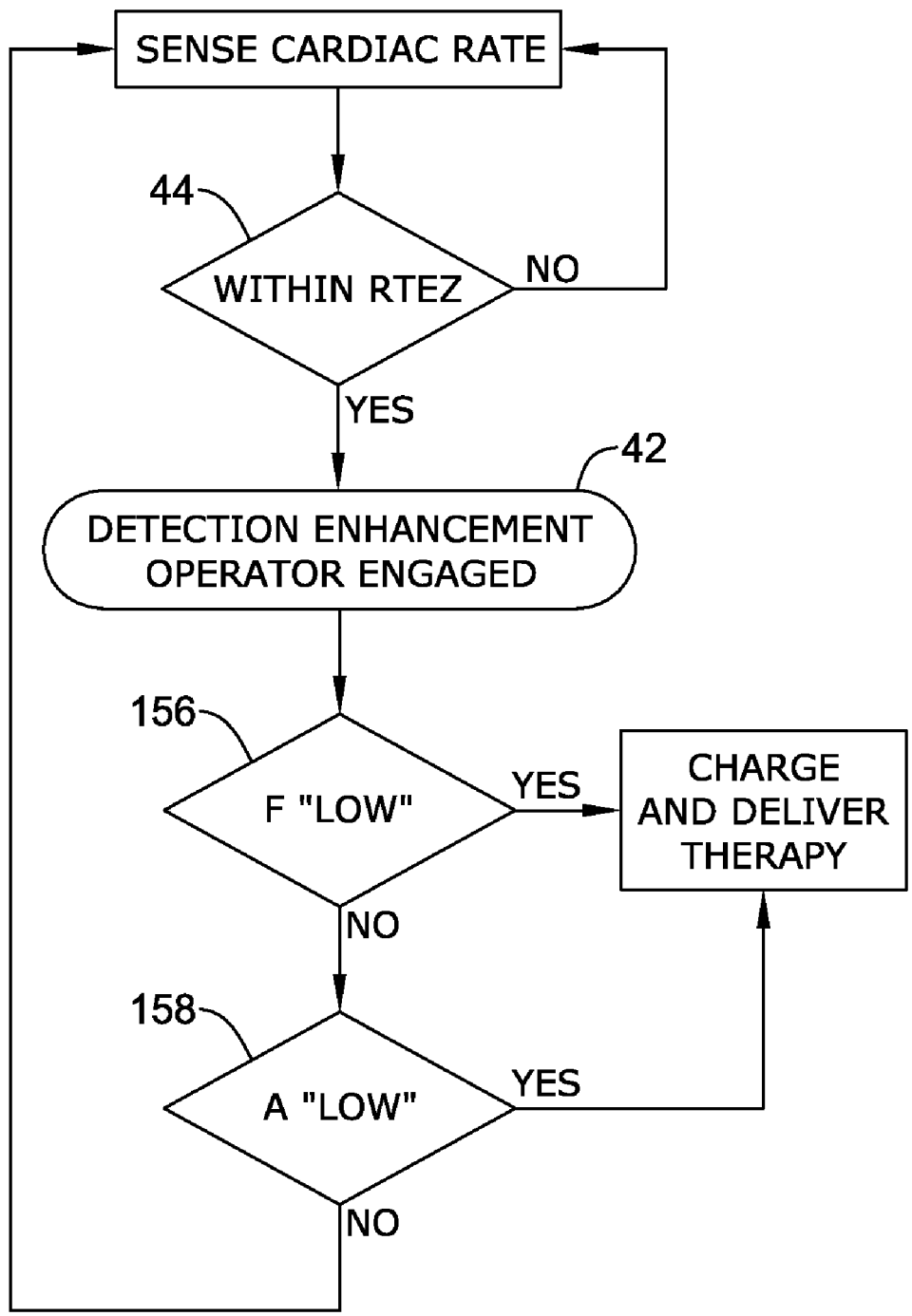

Turning now to FIG. 26, the illustrative method senses the cardiac rate and determines whether the cardiac rate is within the RTEZ 44. If so, the detection enhancement operator 42 is engaged and makes a first layer determination of whether F=LOW, as shown at 156. If so, therapy is delivered. Otherwise, the detection enhancement operator 42 makes a second layer determination of whether A=LOW, as shown at 158. If so, therapy is delivered. If both queries 156, 158 fail, the system returns to sensing the cardiac rate.

Figure 27:
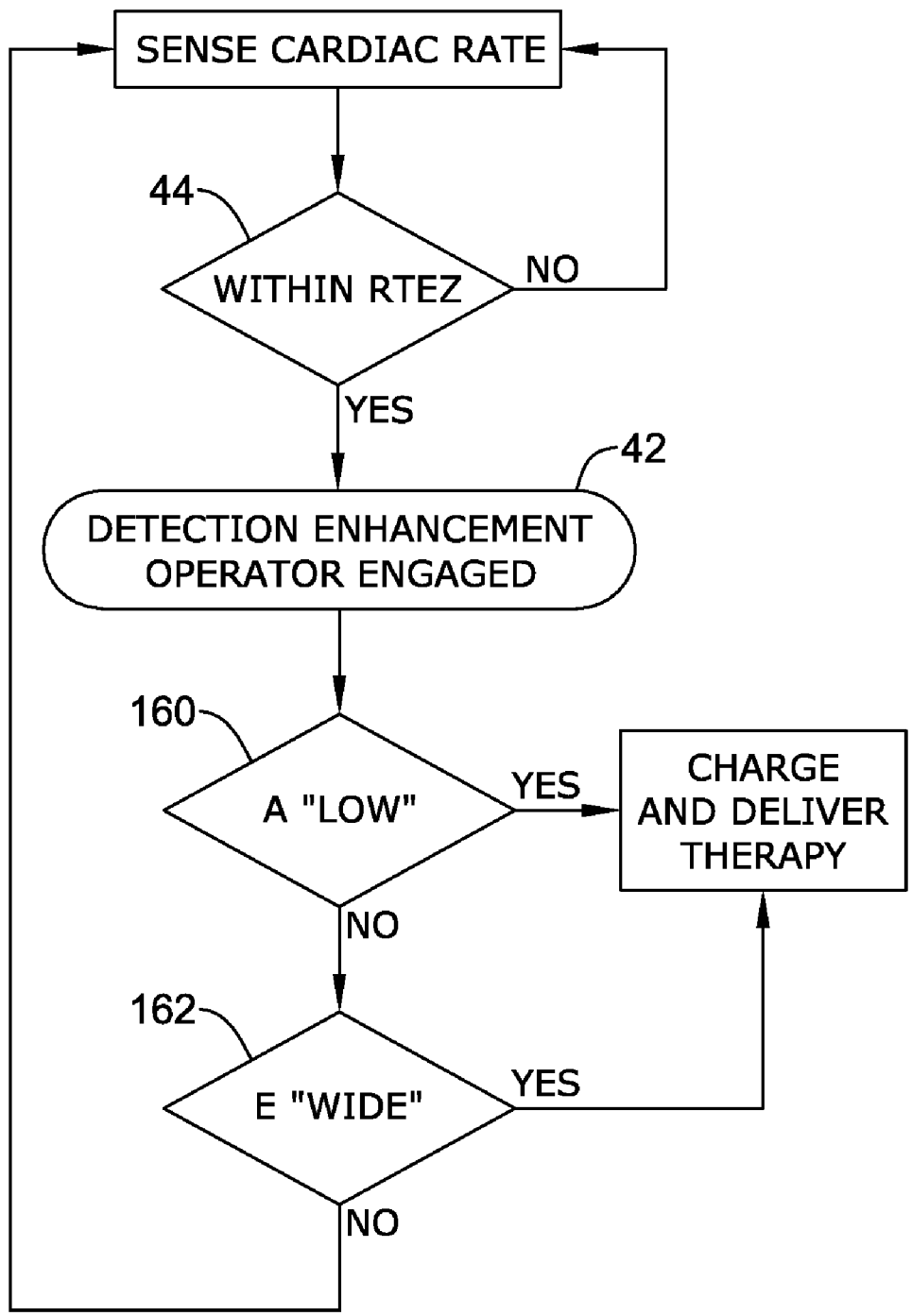

Turning now to FIG. 27, the illustrative method senses the cardiac rate and determines whether the cardiac rate is within the RTEZ 44. If so, the detection enhancement operator 42 is engaged and makes a first layer determination of whether A=LOW, as shown at 160. If so, therapy is delivered. Otherwise, the detection enhancement operator 42 makes a second layer determination of whether E=WIDE, as shown at 162. If so, therapy is delivered. If both queries 160, 162 fail, the system returns to sensing the cardiac rate.

Figure 28:
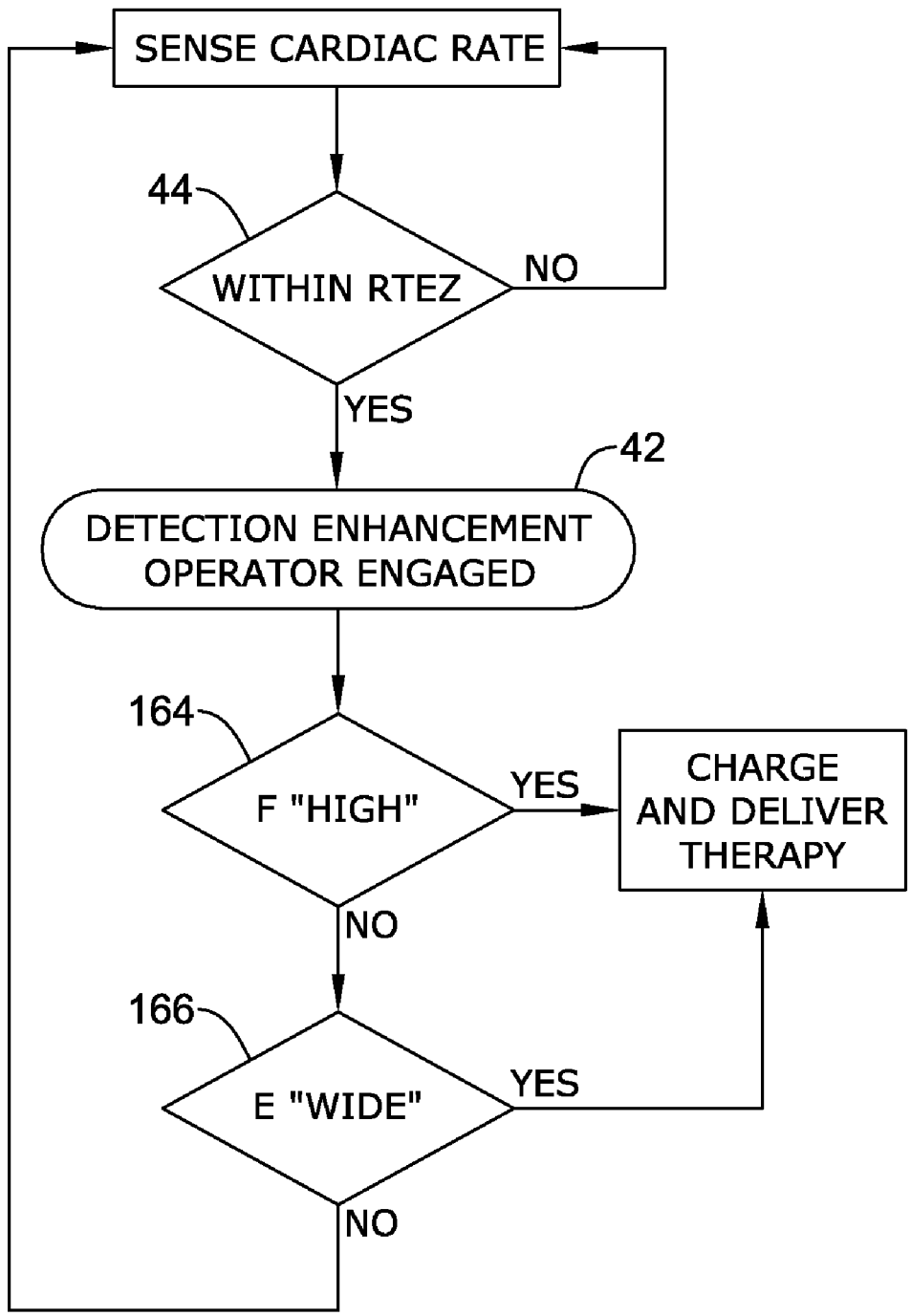

Turning now to FIG. 28, the illustrative method senses the cardiac rate and determines whether the cardiac rate is within the RTEZ 44. If so, the detection enhancement operator 42 is engaged and makes a first layer determination of whether F=HIGH, as shown at 164. If so, therapy is delivered. Otherwise, the detection enhancement operator 42 makes a second layer determination of whether E=WIDE, as shown at 166. If so, therapy is delivered. If both queries 164, 166 fail, the system returns to sensing the cardiac rate.

Figure 29:
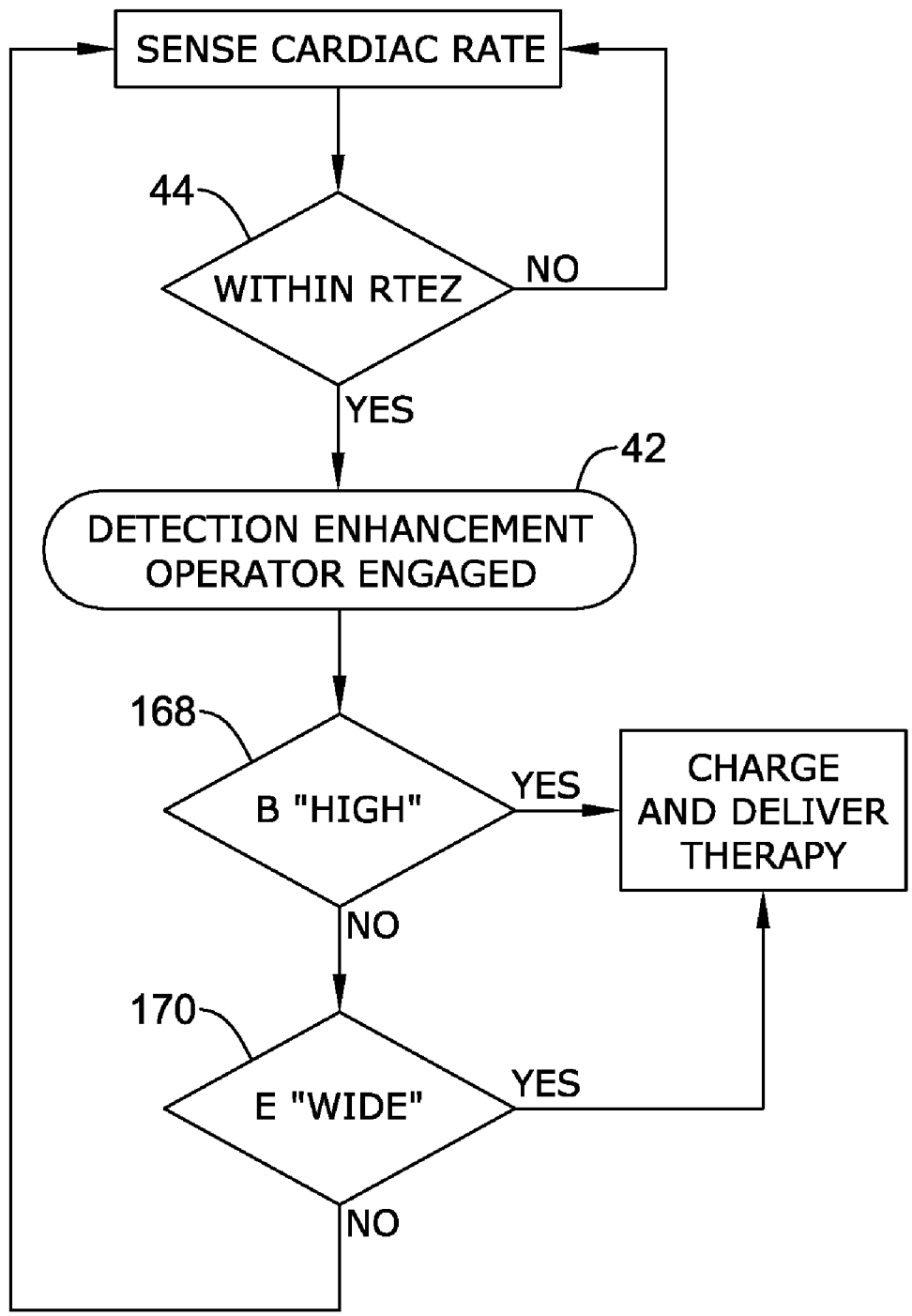

Turning now to FIG. 29, the illustrative method senses the cardiac rate and determines whether the cardiac rate is within the RTEZ 44. If so, the detection enhancement operator 42 is engaged and makes a first layer determination of whether B=HIGH, as shown at 168. If so, therapy is delivered. Otherwise, the detection enhancement operator 42 makes a second layer determination of whether E=WIDE, as shown at 170. If so, therapy is delivered. If both queries 168, 170 fail, the system returns to sensing the cardiac rate.

FIGS. 9 and 14-29 are illustrative examples only; other combinations using the results of Tables 1-3, not specifically identified by these figures, are additionally possible and are contemplated by the present invention.

In addition to cascading one-sided algorithms, ambiguities are also greatly reduced by using a subcutaneous electrode ICD system like the one described above with reference to FIG. 1A, rather than a transvenous system as shown in FIG. 1B. More specifically, ambiguity is reduced in a subcutaneous electrode ICD system because the subcutaneous system is optimized physically and spatially for the collection of far field vector information. The spatial distance between electrodes (e.g., between the first sensing electrode 20 and the canister sensing electrode 16—vector view 1) may enhance visibility of far field vector information. As such, attributes specific to ventricular arrhythmias such as polarity changes or other morphological attributes are readily recognized in subcutaneous ICD systems. This enhanced taxonomy, in turn, affects the propagation of the data assessed using a particular comparison method. Table 4 shows some comparison methods that tease out particular arrhythmias and their corresponding ambiguity percentage using a subcutaneous ICD system. In particular, Table 4 illustrates how the ambiguities percentages using certain comparison methods are reduced using a subcutaneous ICD system.

TABLE 4

| | AF | AT/ST | MVT | PVT | VF |
|---|---|---|---|---|---|
| A | — | — | LOW (8%) | — | — |
| B | — | — | — | — | — |
| C | — | — | HIGH (8%) | — | — |
| D | — | — | — | — | — |
| E | NARROW (13%) | NARROW (13%) | — | — | — |
| F | — | — | — | — | — |
| G | NO (8%) | — | — | YES (8%) | YES (8%) |

Ambiguity can be further eliminated from these comparison methods by observing the same comparison method from additional vector views using a subcutaneous ICD system. As described in detail above, the detection enhancement operator 12 can mathematically compare acquired cardiac complexes (or there vector representations) from two views to their corresponding template views. This configuration enhances the detection enhancement operator's ability to discern supraventricular based arrhythmias from ventricular based arrhythmias. More specifically, it is extremely unlikely that a ventricular based arrhythmia would appear the same as its stored sinus template in both views. In such an instance, at least one of the two views would indicate a morphology change, based on its origination in the ventricle, when compared to the stored sinus templates. Thus, although there may not be a discriminating difference in one view between a ventricular based arrhythmia and a stored sinus template, by examining a second view, the distinction would more likely be pronounced.

By coupling the optimized far field vector sensing of a subcutaneous electrode ICD system with the ability to sense in multiple views, the combination reduces virtually all lingering ambiguity when using a particular comparison method. Moreover, through this combination, only two comparison methods are necessary to discern the supraventricular based arrhythmias from ventricular based arrhythmias. Table 5 shows the resulting comparison methods that tease out particular arrhythmias and their corresponding ambiguity percentage using a subcutaneous ICD system with multiple views. In particular, Table 5 illustrates how the ambiguities percentages are nearly unappreciable using the two comparison methods in a subcutaneous ICD system with multiple views.

TABLE 5

| | AF | AT/ST | MVT | PVT | VF |
|---|---|---|---|---|---|
| A | HIGH (0.1%) | HIGH (0.1%) | LOW (0.3%) | LOW (0.05%) | LOW (0.05%) |
| D | LOW (0.1%) | LOW (0.1%) | LOW (0.2%) | HIGH (0.05%) | HIGH (0.05%) |

In analyzing Table 5, it is surmised that Boolean ANDing comparison method A with comparison method D permits the detection enhancement operator 12 to remove all statistically significant ambiguity from its decision-making process. In particular, ambiguity is virtually eliminated by having the detection enhancement operator evaluate the following—does comparison method A result in a LOW score and (a Boolean AND) does comparison method D result in a HIGH score? A "yes" answer to this Boolean query unambiguously identifies the arrhythmias PVT and VF. Moreover, PVT and VF demonstrate ambiguities of fractional percentages for this evaluation. Additionally, because these arrhythmias require therapy, the device would then be directed to deliver a therapeutic shock following this "yes" answer. A "no" answer to this Boolean query, however, would result in the detection enhancement operator withholding treatment.

Figure 30:
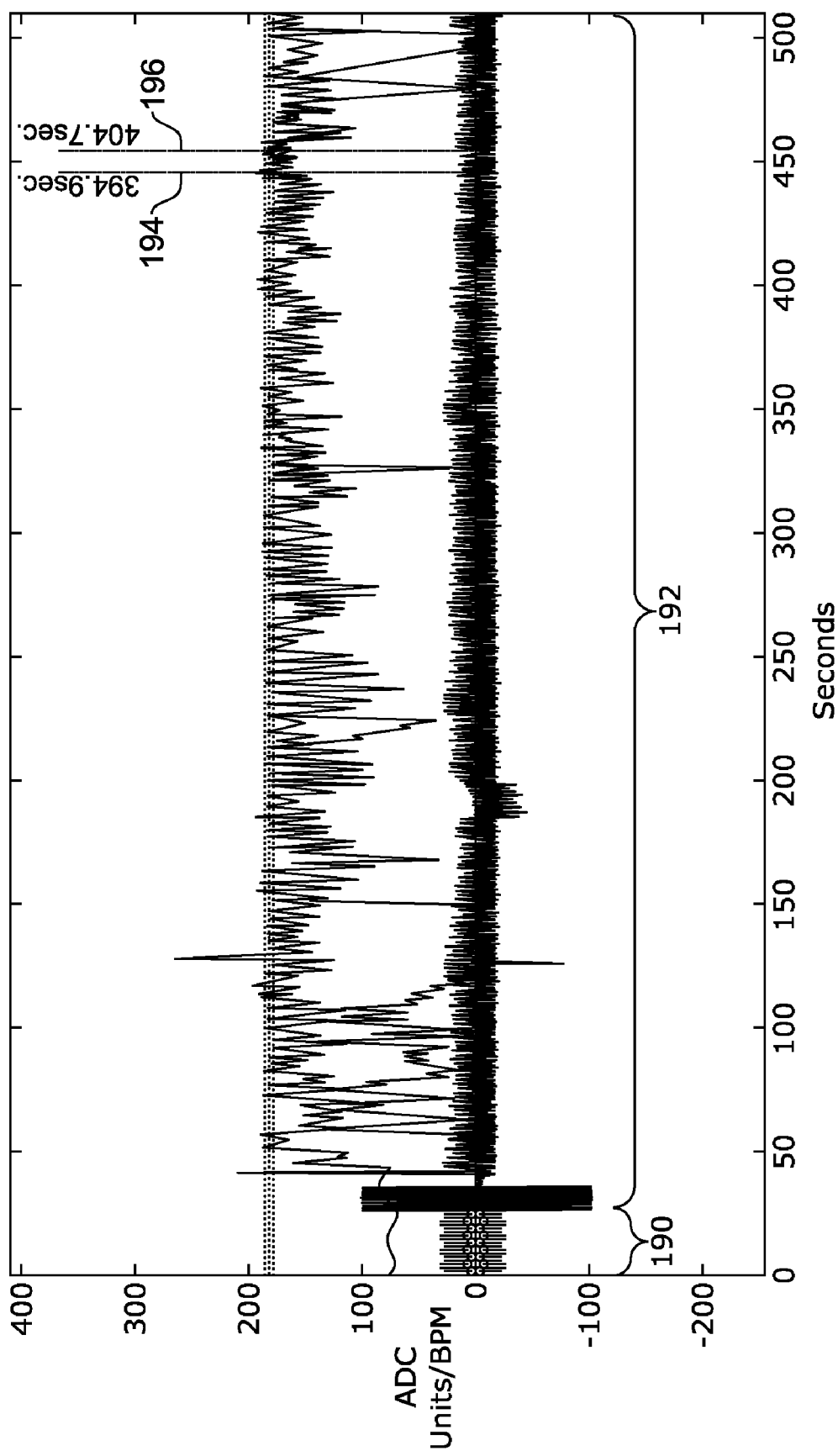

FIGS. 30 and 31 illustrate how the detection enhancement operator 42 may additionally distinguish supraventricular arrhythmias from normal sinus rhythms and ventricular arrhythmias. A supraventricular arrhythmia segment 192 and a normal sinus segment 190 are shown in the electrocardiogram of FIG. 30. Furthermore, the electrocardiogram illustrates that if rate was the only determinative factor in deciding whether to apply or withhold therapy, a patient experiencing such a supraventricular arrhythmia would have been delivered an inappropriate shock. The point in the electrocardiogram where an event is declared using an industrial standard rate based algorithm is shown as lines 194 and 196.

Several embodiments of the present invention greatly reduce the instances of inappropriate shocks such as the one delivered in FIG. 30. For example, a three dimensional representation of both the first and the second layer of questioning 75, 77 of FIG. 9 is depicted in FIG. 31. Comparison methods A, D and E align the three axes of the graph. When the detection enhancement operator 42 evaluates the first and second layer of questioning 75, 77 on the sample electrocardiogram of FIG. 30, a distinct pattern arises. Specifically, both the complexes of the supraventricular arrhythmia segment 190 and the normal sinus rhythm segment 194 populate the same portion of the graph—region 198. Only a few complexes fail to populate this region 198. Moreover, none of these complexes would be capable of initiating therapy because the detection architecture operator 42 further requires an X out of Y filter, which a few stray complexes could not trigger. Thus, in striking comparison to an industry standard rate based algorithm, the illustrative embodiment would not have delivered therapy based on the comparisons performed by the detection enhancement operator 42.

The detection enhancement operator of the present invention possesses tremendous flexibility. The detection enhancement operator 42 can discriminate and detect arrhythmias by using comparison methods (A-G) singly (e.g., A alone), in combination with multiple comparison methods (e.g., A with D), in concert with other parameters (e.g., A with rate above 180 bpm), or in any combination thereof, to direct appropriate therapy in treating arrhythmias. As a result of this flexibility, the timing associated with applying appropriate therapy may be a function of the rhythm identified and the malignancy of the identified rhythm.

Certain arrhythmias, like ventricular fibrillation, will be identified quickly by the detection enhancement operator 42. If these arrhythmias are ones that require therapy, the detection enhancement operator 42, depending on the device requirements, may deliver therapy quickly. For example, the detection enhancement operator 42 may begin charging for therapy delivery within approximately twenty-four beats after sensing the first malignant cardiac complex.

Alternatively, other arrhythmias require greater assessment. The detection enhancement operator 42 may evaluate multiple comparison methods, comparison methods in cascading fashion, different vector views, or a combination thereof prior to discerning a particular arrhythmia. For these more complicated cardiac complexes, the detection enhancement operator 42 is capable of evaluating when to begin preparing for therapy delivery based on the malignancy of the arrhythmia it is discriminating between. If the malignant nature of the arrhythmia being discriminated between is high, the detection enhancement operator 42 may begin charging for therapy delivery before finally assessing the arrhythmia. If, however, the detection enhancement operator 42 perceives the arrhythmia being assessed is most likely a supraventricular event, i.e., a non-life threatening rhythm, the detection enhancement operator 42 may withhold therapy delivery until an assessment is finally determined.

For the majority of rhythms occurring in patients receiving this type of device, the detection enhancement operator 42 of the present invention is capable of assessing and treating a life threatening arrhythmia quickly. For the remainder of the rhythm disorders, the detection architecture of the present invention will take additional time to run through the various comparison methods and cascades in order to enhance specificity. This, in fact, makes clinical sense; where the rapidity and aggressiveness of the device intervention matches the malignancy of the arrhythmia.

The present invention, in some embodiments, is also embodied by operational circuitry including select electrical components provided within the canister 12 (FIG. 1A) or canister 32 (FIG. 1B). In such embodiments, the operational circuitry may be configured to enable the above methods to be performed. In some similar embodiments, the present invention may be embodied in readable instruction sets such as a program encoded in machine or controller readable media, wherein the readable instruction sets are provided to enable the operational circuitry to perform the analysis discussed in the above embodiments. Further embodiments may include a controller or microcontroller adapted to read and execute the above methods. These various embodiments may incorporate the illustrative methods shown in FIGS. 9 and 14-29, for example.

The following illustrative embodiments are explained in terms of operational circuitry. The operational circuitry may be configured to include such controllers, microcontrollers, logic devices, memory, and the like, as selected, needed, or desired, for performing the method steps for which each is adapted.

An illustrative embodiment may comprise an ICD comprising a lead electrode assembly including a number of electrodes, and a canister housing operational circuitry; wherein the lead electrode assembly is coupled to the canister and the operational circuitry is configured to perform a method for discriminating between arrhythmias which are appropriate for therapy. In the illustrative embodiment, the method comprises receiving a cardiac complex using implanted electrodes, obtaining a cardiac rate, determining whether the cardiac rate either exceeds a first threshold but does not exceed a second threshold, or exceeds the second threshold; and, if the cardiac rate exceeds the second threshold, directing therapy to the heart; or if the cardiac rate exceeds the first threshold but does not exceed the second threshold, directing further analysis of the cardiac complex to determine whether therapy is indicated. In some related embodiments, the further analysis includes comparison of the cardiac complex to a template. For one such related embodiment, the comparison includes a correlation waveform analysis. In another related embodiment, the template is formed by averaging a number of recent cardiac complexes. In yet another related embodiment, the template is a static template. The further analysis may also include a determination of a correlation between the cardiac complex and a template and comparison of the correlation for the cardiac complex to correlations for a number of recent cardiac complexes. Also, the further analysis may include a QRS complex width measurement, a determination of whether the cardiac rate accelerated significantly, or a determination of the interval rate stability between cardiac complexes.

Yet another embodiment includes an ICD comprising a lead electrode assembly including a number of electrodes and a canister housing operational circuitry, wherein the lead electrode assembly is coupled to the canister and the operational circuitry is configured to perform a method of cardiac analysis. For the illustrative embodiment, the method may include receiving a cardiac complex from an implanted electrode pair, analyzing the cardiac complex to determine whether a patient is likely experiencing an arrhythmia, and comparing a portion of the cardiac complex to a template by performing a mathematical calculation between the cardiac complex and the template, wherein the comparing step is performed only if it is determined that the patient is likely experiencing an arrhythmia. In related embodiments, the step of analyzing the cardiac complex to determine whether an arrhythmia likely includes estimating a cardiac rate and comparing the cardiac rate to a threshold value. Some embodiments may also include updating the template using data from the cardiac complex. The mathematical calculation may include a correlation waveform analysis. In a further embodiment, the step of receiving a cardiac complex from an implanted electrode pair includes receiving a first electrical signal from a first combination of electrodes, receiving a second electrical signal from a second combination of electrodes, comparing the first electrical signal to the second electrical signal to determine which electrical signal is more amenable to data analysis, and using the electrical signal that is more amenable to data analysis as the cardiac complex for comparison with the template. In another embodiment, the device may further execute a method step including selecting a template for use in the comparison step in response to an observed event occurring prior to the receipt of the cardiac complex. Such embodiments may observe and/or treat a monomorphic ventricular tachycardia, a polymorphic ventricular tachycardia, or ventricular fibrillation.

An illustrative embodiment includes an ICD comprising a lead electrode assembly including a number of electrodes and a canister housing operational circuitry, wherein the lead electrode assembly is coupled to the canister and the operational circuitry is configured to perform a method of discriminating between cardiac arrhythmias. The method the operational circuitry is configured to perform may include receiving a first electric signal between a first electrode pair, analyzing the first electric signal to calculate a cardiac rate for a patient, comparing the cardiac rate to first and second thresholds, and selecting one of the following options: a) if the cardiac rate is below the first threshold, advancing to a next iteration of the method by receiving a second electric signal between the first electrode pair, the second electric signal coming temporally after the first electric signal; or b) if the cardiac rate is above the second threshold, determining that therapy should be delivered to the patient; or c) advancing into a subroutine for enhanced analysis, wherein the subroutine for enhanced analysis includes comparing a portion of the first electric signal to a template.

Yet another embodiment includes an ICD comprising a lead electrode assembly including a number of electrodes and a canister housing operational circuitry, wherein the lead electrode assembly is coupled to the canister and the operational circuitry is configured to perform a method of discriminating between cardiac rhythms comprising receiving a cardiac complex, determining that an arrhythmia is likely, analyzing the cardiac complex using a first metric to determine whether a malignant arrhythmia is occurring and, if so, determining that therapy is indicated, if not, then analyzing the cardiac complex using a second metric to determine whether a malignant arrhythmia is occurring and, if so, determining that treatment is indicated. In a further embodiment, the operational circuitry is configured such that both the first metric and the second metric are calculated using the cardiac complex, wherein the cardiac complex is captured using two electrodes.

Another embodiment includes an ICD comprising a lead electrode assembly including a number of electrodes and a canister housing operational circuitry, wherein the lead electrode assembly is coupled to the canister and the operational circuitry is configured to perform a method of signal analysis comprising receiving a first cardiac complex from a first implanted electrode pair disposed to capture electrical information related to ventricular activity along a first sensing vector, receiving a second cardiac complex from a second implanted electrode pair disposed to capture electrical information related to ventricular activity along a second sensing vector, generating a first metric related to the first cardiac complex, generating a second metric related to the second cardiac complex, and comparing the first metric to the second metric to determine whether a ventricular originating arrhythmia is occurring. In further embodiments, the first cardiac complex and the second cardiac complex are substantially temporally related, the first sensing vector and the second sensing vector are placed at an angle of greater than 45 degrees with respect to one another, the first electrode pair includes first and second electrodes, and the second electrode pair includes the second electrode and a third electrode, and/or the first electrode pair and the second electrode pair are disposed to capture far-field signals for atrial and ventricular events.

Another embodiment includes an ICD comprising a lead electrode assembly including a number of electrodes and a canister housing operational circuitry, wherein the lead electrode assembly is coupled to the canister and the operational circuitry is configured to perform a method of monitoring cardiac function as part of the operation of an implantable cardiac treatment device. For the illustrative embodiment, the operational circuitry may be configured to perform a method including receiving a cardiac complex from first and second implanted electrodes, comparing the cardiac complex to a template to determine whether therapy is indicated, wherein the template is a dynamically changing template formed using a number of recently sensed cardiac complexes. In a further embodiment, the step of comparing the cardiac complex to a template includes performing a correlation waveform analysis to generate a correlation coefficient, and comparing the correlation coefficient to a threshold.

Another embodiment includes an ICD comprising a lead electrode assembly including a number of electrodes and a canister housing operational circuitry, wherein the lead electrode assembly is coupled to the canister and the operational circuitry is configured to perform a method of discriminating between cardiac rhythms comprising receiving a cardiac complex from implanted electrodes, obtaining a cardiac rate and determining whether an arrhythmia is likely; and, if so: (a) analyzing the cardiac complex using a first mathematical determination to yield a first result, and comparing the first result to a first threshold to yield a first Boolean value; (b) analyzing the cardiac complex using a second mathematical determination to yield a second result, and comparing the second result to a second threshold to yield a second Boolean value; and (c) performing a first Boolean logic function using at least one of the first Boolean value and the second Boolean value to determine whether therapy is needed. In a further embodiment, the operational circuitry is configured such that the first mathematical determination is a correlation between a static template and the cardiac complex, the second mathematical determination is a variability of correlations of several recent cardiac complexes compared to a dynamic template, the Boolean logic function observes whether the first Boolean value is zero and the second Boolean value is one, and, if the Boolean logic function yields a one, it is determined that therapy is needed. For another embodiment, the operational circuitry is configured so the first mathematical determination is a correlation between a static template and the cardiac complex, the second mathematical determination is a variability of correlations of several recent cardiac complexes compared to a static template, the Boolean logic function observes whether the first Boolean value is zero and the second Boolean value is one, and, if the Boolean logic function yields a one, it is determined that therapy is needed.

In another embodiment using such Boolean logic, the operational circuitry is further configured such that the first mathematical determination is a correlation between a static template and the cardiac complex, the second mathematical determination is an analysis of an interval rate stability for a number of recent cardiac complexes, the Boolean logic function observes whether the first Boolean value is zero and the second Boolean value is one, and, if the Boolean logic function yields a one, it is determined that therapy is needed. An illustrative embodiment includes operational circuitry configured so that the first mathematical determination is a variability of correlations of several recent cardiac complexes compared to a dynamic template, the second mathematical determination is an analysis of the width of the cardiac complex, the Boolean logic function observes whether the first Boolean value is one and the second Boolean value is one, and, if the Boolean logic function yields a one, it is determined that therapy is needed. Yet another embodiment executes a method wherein the first mathematical determination is a correlation between a static template and the cardiac complex, the second mathematical determination is a variability of correlations of several recent cardiac complexes compared to a static template, the Boolean logic function observes whether the first Boolean value is zero and the second Boolean value is zero, and, if the Boolean logic function yields a one, it is determined that therapy is needed.

Yet another embodiment using the noted Boolean logic includes operational circuitry further configured such that the method includes analyzing the cardiac complex using a third mathematical determination to yield a third result, and comparing the third result to a third threshold to yield a third Boolean value, and performing a second Boolean logic function using at least one of the first, second, and/or third Boolean values to determine whether therapy is needed.

Another embodiment includes an ICD comprising a lead electrode assembly including a number of electrodes and a canister housing operational circuitry, wherein the lead electrode assembly is coupled to the canister and the operational circuitry is configured to perform a method of discriminating between cardiac rhythms comprising receiving a cardiac complex from implanted electrodes, obtaining a cardiac rate and determining whether an arrhythmia is likely; and, if so: (a) analyzing the cardiac complex using a first metric to determine whether a malignant arrhythmia is occurring and, if so, determining that therapy is indicated; and (b) if not, then analyzing the cardiac complex using a second metric to determine whether a malignant arrhythmia is occurring and, if so, determining that treatment is indicated. In further embodiments, the first metric is a comparison of the cardiac complex width to a threshold wherein, if the width is greater than the threshold value it is determined that a malignant arrhythmia is occurring, wherein the second metric is a correlation between the cardiac complex and a template, wherein if the correlation is low then it is determined that a malignant arrhythmia is occurring, wherein the template may be static or dynamic. In another embodiment, the second metric is a comparison of the correlation of the cardiac complex and a template to the correlation of a number of recent cardiac complexes to the template to yield a variability, wherein if the variability is high then it is determined that a malignant arrhythmia is occurring. Again, the template may be either static or dynamic. In another embodiment, the first metric is a comparison of a threshold to a correlation between the cardiac complex and a template wherein, if the correlation is low, then it is determined that a malignant arrhythmia is occurring. The template may be static or dynamic. In one embodiment, the first metric is a threshold comparison with respect to a correlation to a static template, and the second metric is a comparison of a threshold to a correlation between the cardiac complex and a dynamic template wherein, if the correlation is low, then it is determined that a malignant arrhythmia is occurring. In yet another embodiment, the second metric is a determination of the variability of the correlation between the cardiac complex and the template to correlations between recent cardiac complexes and the template wherein, if the variability is high, then it is determined that a malignant arrhythmia is occurring.

Numerous characteristics and advantages of the invention covered by this document have been set forth in the foregoing description. It will be understood, however, that this disclosure is, in many aspects, only illustrative. Changes may be made in details, particularly in matters of shape, size and arrangement of parts without exceeding the scope of the invention. The invention's scope is defined, of course, in the language in which the claims are expressed.

What is claimed is:

1. A method of cardiac signal analysis in an implantable medical device having at least a housing containing operational circuitry and a plurality of electrodes coupled to the operational circuitry for capturing cardiac signals comprising:
   capturing a cardiac event using at least first and second vector views from the electrodes;
   analyzing the captured cardiac event using a first method of analysis by comparing the captured cardiac event as seen from the first vector view to a stored sinus template of the first vector view;
   analyzing the captured cardiac event using a second method of analysis including comparing the captured cardiac event as seen from the second vector view to a cardiac event just previous to the captured cardiac event, as seen from the second vector view;
   identifying whether an arrhythmia is likely occurring and, if so, distinguishing a supraventricular arrhythmia from a ventricular originating arrhythmia using results from the first and second methods to determine whether a ventricular originating arrhythmia is occurring; and
   if a ventricular originating arrhythmia is occurring, directing cardiac defibrillation therapy to the patient.

2. The method of claim 1 wherein the plurality of electrodes includes a first electrode disposed on the surface of the housing, and the implantable medical device comprises a lead attached to the housing, the lead including at least second and third electrodes, wherein the lead is disposed only subcutaneously in the patient.

3. The method of claim 1 wherein the plurality of electrodes includes a first electrode disposed on the surface of the housing, and the implantable medical device comprises a lead attached to the housing, the lead including at least second and third electrodes, wherein the lead is disposed transvenously in the patient such that at least one electrode is disposed internal to the patient's heart.

4. The method of claim 1 wherein:
   the first method of analysis further comprises comparing the captured cardiac events as seen from second first vector view to a stored sinus template of the second vector view; and
   the second method of analysis further comprises comparing the captured cardiac event as seen from the first vector view to the cardiac event, as seen from the first vector view, just previous to the captured cardiac event.

5. The method of claim 4 wherein the step of identifying whether an arrhythmia is likely occurring includes estimating cardiac rate and comparing the rate to a threshold, wherein if the cardiac rate exceeds the threshold, an arrhythmia is likely occurring.

6. The method of claim 4 wherein:
   the first method of analysis generates, for each detected event, correlation scores indicating similarity between the stored sinus template and the detected event in each vector view;
   the second method of analysis further comprises repeatedly comparing a set of captured cardiac events to immediately previous captured cardiac events using both the first and second vector views to establish sets of results for each of the first and second vector views and calculating a variability for the sets of results, and
   if an arrhythmia is likely occurring, then the step of distinguishing a supraventricular arrhythmia from a ventricular originating arrhythmia includes determining that a ventricular originating arrhythmia is occurring if, for either of the first or second vector views, both a low correlation score is found in the first method and a high variability is found in the second method.

7. The method of claim 1 wherein the step of identifying whether an arrhythmia is likely occurring includes estimating cardiac rate and comparing the rate to a threshold, wherein if the cardiac rate exceeds the threshold, an arrhythmia is likely occurring.

8. An implantable cardiac stimulus device system comprising:
   a housing containing operational circuitry including at least a battery and a controller, the operational circuitry configured to observe electrical cardiac activity of the patient and, if determined necessary, to provide electrical cardiac stimulus to a patient if implanted in the patient; and a lead electrode assembly comprising at least one electrode for use in at least one of observing electrical cardiac activity and/or delivering electrical cardiac stimulus to a patient;

wherein the operational circuitry is configured to observe electrical cardiac activity as follows in order to determine whether electrical cardiac stimulus is indicated:

capture a cardiac event using at least first and second vector views defined by electrodes included in the lead electrode assembly and/or located on the canister;

analyze the captured cardiac event using a first method of analysis which includes comparing the captured cardiac event as seen from the first vector view to a stored sinus template of the first vector view;

analyze the captured cardiac event using a second method of analysis including comparing the captured cardiac event as seen from the second vector view to a cardiac event just previous to the captured cardiac event as seen from the second vector view;

identify whether an arrhythmia is likely occurring and, if so, distinguish a supraventricular arrhythmia from a ventricular originating arrhythmia using results from the first and second methods to determine whether a ventricular originating arrhythmia is occurring; and determine electrical cardiac stimulus is indicated if a ventricular originating arrhythmia is occurring.

9. The system of claim 8 wherein operational circuitry is configured such that:

the first method of analysis further comprises comparing the captured cardiac events as seen from second first vector view to a stored sinus template of the second vector view; and the second method of analysis further comprises comparing the captured cardiac event as seen from the first vector view to the cardiac event, as seen from the first vector, view just previous to the captured cardiac event.

10. The system of claim 9 wherein the operational circuitry is configured such that, in order to identify whether an arrhythmia is likely occurring, the operational circuitry estimates cardiac rate and compares the rate to a threshold, wherein if the cardiac rate exceeds the threshold, the operational circuitry will identify that an arrhythmia is likely occurring.

11. The system of claim 9 wherein the operational circuitry is configured such that:

the first method of analysis generates, for each detected event, correlation scores indicating similarity between the stored sinus template and the detected event in each vector view;

the second method of analysis further comprises repeatedly comparing a set of captured cardiac events to immediately previous captured cardiac events using both the first and second vector views to establish sets of results for each of the first and second vector views and calculating a variability for the sets of results, and if the operational circuitry determines an arrhythmia is likely occurring, then the operational circuitry determines whether a high variability is found in the second method and a low correlation score form the first method for either of the first or second vector views and, if so, the operational circuitry determines a ventricular arrhythmia is occurring.

12. The system of claim 8 wherein the operational circuitry is configured such that, in order to identify whether an arrhythmia is likely occurring, the operational circuitry estimates cardiac rate and compares the rate to a threshold, wherein if the cardiac rate exceeds the threshold, the operational circuitry will identify that an arrhythmia is likely occurring.

* * * * *